(12) United States Patent
Omi et al.

(10) Patent No.: US 8,767,062 B2
(45) Date of Patent: Jul. 1, 2014

(54) FACE IMAGING SYSTEM AND METHOD FOR CONTROLLING THE FACE IMAGING SYSTEM

(75) Inventors: Takuhiro Omi, Anjo (JP); Taito Watanabe, Obu (JP)

(73) Assignee: Denso Corporation, Kariya (JP)

( * ) Notice: Subject to any disclaimer, the term of this patent is extended or adjusted under 35 U.S.C. 154(b) by 285 days.

(21) Appl. No.: 13/356,988

(22) Filed: Jan. 24, 2012

(65) Prior Publication Data

US 2012/0188355 A1    Jul. 26, 2012

(30) Foreign Application Priority Data

Jan. 25, 2011  (JP) .................................. 2011-12485

(51) Int. Cl.
*H04N 7/18* (2006.01)

(52) U.S. Cl.
USPC ............ 348/77; 348/78; 348/362; 348/222.1; 348/241; 348/E7.085; 382/103; 382/118

(58) Field of Classification Search
None
See application file for complete search history.

(56) References Cited

U.S. PATENT DOCUMENTS

| 7,801,433 B2 | 9/2010 | Funaki et al. |
| 2008/0309777 A1 | 12/2008 | Aoyama |
| 2009/0028440 A1* | 1/2009 | Elangovan et al. ........... 382/216 |

FOREIGN PATENT DOCUMENTS

| JP | 2005-323180 | 11/2005 | |
| JP | 2005323180 A | * 11/2005 | ............. H04N 5/238 |
| JP | 2008-046255 | 2/2008 | |
| JP | 2009-294781 | 12/2009 | |
| JP | 2009294781 A | * 12/2009 | |
| JP | 4419609 | 2/2010 | |

OTHER PUBLICATIONS

Office Action issued Dec. 7, 2012 in corresponding Japanese Application No. 2011-012485 with English translation.
Office action dated Dec. 4, 2013 in corresponding Chinese Application No. 2012 10021056.6.

* cited by examiner

*Primary Examiner* — Christopher S Kelley
*Assistant Examiner* — Kaitlin A Retallick
(74) *Attorney, Agent, or Firm* — Harness, Dickey & Pierce, PLC

(57) ABSTRACT

A projection unit projects light to a predetermined projection region in which a user's face is supposed to be located. An imaging unit images a region including the projection region projected with light from the projection unit. A proximity detection unit detects that the user's face approaches the projection unit. A first projection control unit causes the projection unit to stop or dim projection of light when the proximity detection unit detects the approach of the user's face.

11 Claims, 15 Drawing Sheets

FACE IMAGING SYSTEM AND METHOD FOR CONTROLLING THE FACE IMAGING SYSTEM

CROSS REFERENCE TO RELATED APPLICATIONS

This application is based on Japanese Patent Application No. 2011-12485 filed on Jan. 25, 2011, the contents of which are incorporated in their entirely herein by reference.

TECHNICAL FIELD

The present invention relates to a face imaging system configured to project light to a user's face and to image the user's face. The present invention further relates to a method for controlling the face imaging system.

BACKGROUND

A known driver monitor system is configured to monitor a driver of a vehicle in order to detect the direction of the driver's face, the opening state of driver's eyes, and the like FIG. 13 shows an overview of a driver monitor system 100 according to a prior art. The driver monitor system 100 includes a projector 102 configured to project light, such as near-infrared light, to a projection region 101 in order to image a driver's face located in the projection region 101 clearly regardless of day or night. The driver monitor system 100 further includes a camera 103 configured to photograph an image of the projection region 101 projected with light from the projector 102. An imaging control unit 104 controls a gain, an exposure time (exposure timing), and the like of the camera 103. In addition, a projection control unit 105 controls a light strength, a projection timing, and the like of the projector 102. The photographic image captured by the camera 103 is sent to an image processing unit 106. The image processing unit 106 implements a predetermined image processing on the photographic image thereby to detect a face region corresponding to the driver's face. Thus, the information on the detected driver's face region is utilized by various systems 107 such as a system for avoiding drowsy driving, a system for avoiding inattentive driving, and the like. Specifically, the various systems 107 detect the direction of the driver's face, the opening state of the driver's eyes, and the like, according to, for example, the face region. The various systems 107 further implement a processing, such as a warning processing, according to the detection result.

As described above, a conventional face imaging system includes a projector (projection unit) configured to project light in a predetermined projection region, in which a driver's face is located, and a camera (imaging unit) configured to photograph an image in the projection region (see, for example, publication of Japanese patent No. 4419609).

It is noted that, in the conventional face imaging system, the projector continues projection of light even when a face of a user, such as a driver, does not exist in the projection region or even when the face existing in the projection region cannot be detected. Therefore, in such a conventional system, when a user looks into a projector suddenly or when a user approaches the projector too closely, the light from the projector may cause eyestrain in the user's eyes. In particular, pupils of the user's eyes hardly expand and contract when projected with near-infrared light from the projector, compared with a case when being projected with visible light.

Therefore, the user's eyes may cause severe eyestrain when being projected with near-infrared light.

SUMMARY

In view of the foregoing and other problems, it is an object of the present invention to produce a face imaging system configured to restrain user's eyes from causing eye strain when the user looks into a projector suddenly and when the user approaches the projector too closely. It is an object of the present invention to produce a method for controlling the face imaging system.

According to an aspect of the present invention, a face imaging system comprises projection unit configured to project light to a predetermined projection region in which a user's face is supposed to be located. The face imaging system further comprises imaging unit configured to image a region including the projection region projected with light from the projection unit. The face imaging system further comprises a proximity detection unit configured to detect approach of the user's face relative to the projection unit. The face imaging system further comprises a first projection control unit configured to cause the projection unit to stop or dim projection of light when the proximity detection unit detects approach of the user's face.

According to another aspect of the present invention, a method for controlling a face imaging system including a projection unit and an imaging unit, the method comprises causing the projection unit to project light to a projection region in which a user's face is supposed to be located. The method further comprises causing the imaging unit to image the projection region, the imaging unit configured to cause blur in a region corresponding to an object approaching the projection unit. The method further comprises determining whether the imaged projection region has blur caused by the imaging unit. The method further comprises detecting approach of the user's face relative to the projection unit on determination that the imaged projection region has blur. The method further comprises causing the projection unit to stop or dim projection of light on detection of approach of the user's face.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION

First Embodiment

Figure 1:
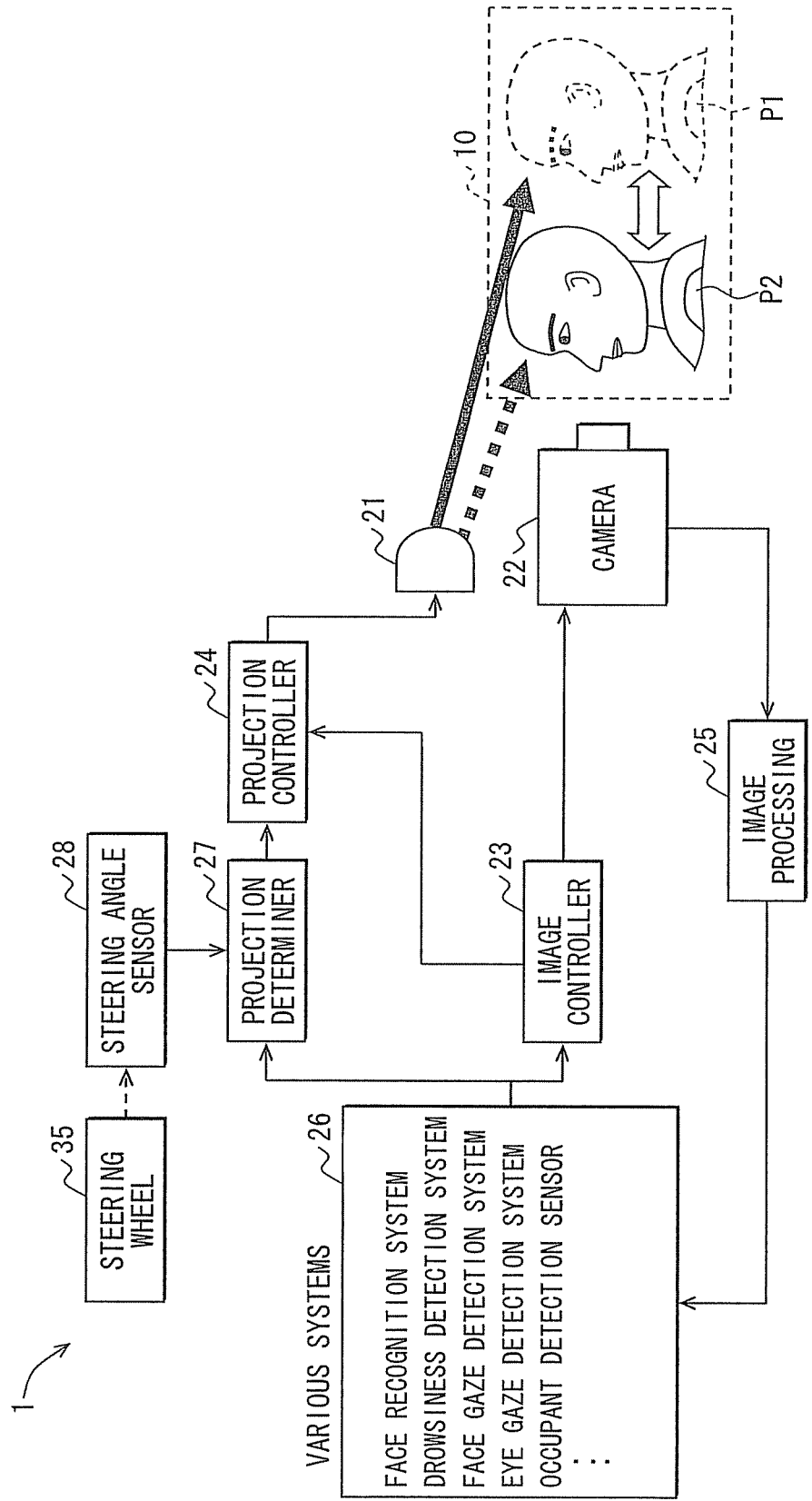
FIG. 1 is a block diagram showing a driver monitor system.

As follows, a face imaging system according to the first embodiment will be described with reference to drawings. In the following embodiment, the face imaging system is applied to a driver monitor system 1 configured to monitor a driver of a vehicle. FIG. 1 shows an overview of the driver monitor system 1 according to the present embodiment. The driver monitor system 1 includes a projector 21, a camera 22, an imaging control unit 23, a projection control unit 24, an image processing unit 25, various systems 26, a projection determination unit 27, and a steering angle sensor 28.

The projector 21 is configured to project light to a lighting region predetermined as a region, in which the face of a driver is located. Specifically, the lighting region is, for example, a peripheral region 10 (driver's seat peripheral region) around a driver's seat (not shown). In the driver's seat peripheral region 10, the driver's face is at a position P1 when not approaching the projector 21, and the driver's face is at a position P2 when approaching the projector 21. FIG. 1 shows the driver's seat peripheral region 10 when being viewed from the lateral side for convenience to illustrate the positions P1 and P2. It is noted that, the driver's seat peripheral region 10 is actually the region shown by the images of FIG. 5A-5D. The projector 21 is located at the position and directed at the projection angle to enable projection of light toward the driver's seat peripheral region 10. Specifically, for example, the projector 21 may be mounted on an upper surface of a steering column of a steering wheel 35 equipped ahead of the driver's seat for steering the vehicle, as shown in FIG. 1. The projector 21 may be built in the camera 22. The projector 21 is configured to project light at a wavelength including near-infrared light to enable the camera 22 to image clearly regardless of daytime or nighttime and not to feel a driver dazzling.

Figure 3:
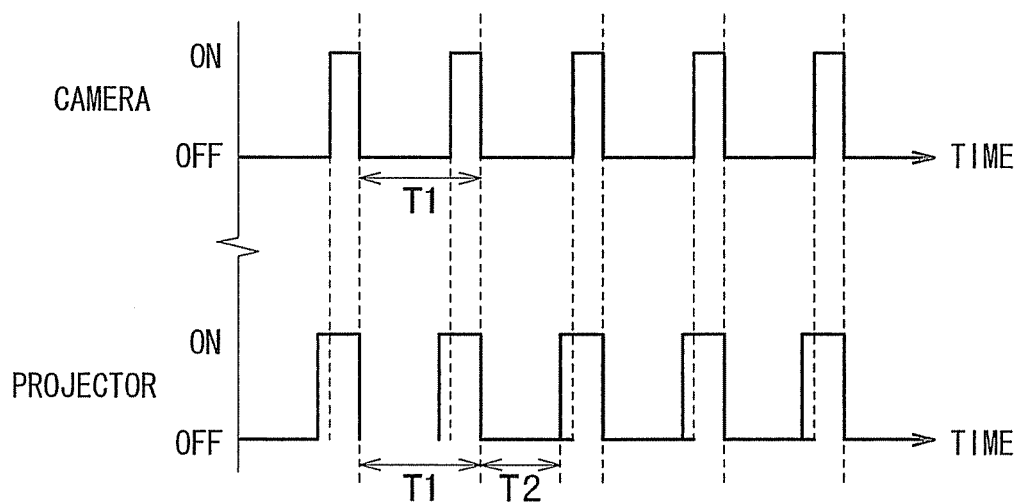
FIG. 3 is a time chart showing a drive timing of the camera and a drive timing of a projector of the driver monitor system.

The projector 21 is controlled by the projection control unit 24. Specifically, the projection control unit 24 is configured to control the strength, the projection timing, and the like of the light projected from the projector 21 according to an imaging condition of the camera 22, the posture of the driver, an environment light, and the like to enable the camera 22 to take a clear image. More specifically, the projection control unit 24 is configured to control the strength and the projection time of the light projected from the projector 21 to satisfy, for example, the exempt level of the IEC standard (IEC 62471). The IEC standard is an international standard established by the International Electrotechnical Commission (IEC). The projection control unit 24 controls activation and deactivation (ON/OFF: projection timing) of the projector 21 according to the exposure timing of the camera 22. FIG. 3 includes the upper time chart representing the exposure timing of the camera 22 and the lower time chart representing the projection timing of the projector 21. As shown in FIG. 3, the projection control unit 24 switches activation and deactivation (ON/OFF) of the projector 21 in the shape of a pulse to synchronize the operation of the projector 21 with the pulse driving power of the shutter of the camera 22. That is, light is projected from the projector 21, while imaging is implemented by the camera 22.

It is noted that, the term of "synchronize" does not necessarily mean exact coincidence among the start timing and the end timing of projection of the projector 21, the end timing and the start timing of exposure of the camera 22. Specifically, when the projector 21 implements projection of light, in general, the projection has a time delay between the time point of a projection instruction and the time point when the projected light rises to its target value. In consideration of this, the projection instruction may be caused slightly earlier than the exposure timing. In addition, the projection has a time delay before the projected light decays to its target value. Therefore, the projection (illumination) may still continue after the end of exposure of the camera 22. These cases are also included in the term of "synchronize." In the present embodiment, as shown in FIG. 3, projection of the projector 21 is started in advance of exposure of the camera 22. The end timing of projection of the projector 21 is set at substantially the same time point as the end timing of exposure of the camera 22. Therefore, the projection cycle T1 (time period between end timings) of the projector 21 is set at substantially the same time period as the projection cycle T1 of the camera 22. The end timing of projection of the projector 21 may be slightly delayed relative to the end timing of exposure of the camera 22. In a specific state, the projection control unit 24 may cause the projector 21 to project light, which does not synchronize with the exposure timing of the camera 22.

The camera 22 includes an image sensor, such as a CCD image sensor and/or a CMOS image sensor for imaging the driver's seat peripheral region 10 where light is projected from the projector 21. The camera 22 is mounted at a position where the camera 22 is enabled to image the driver's seat peripheral region 10. Specifically, the camera 22 may be located on the upper surface of the steering column of the steering wheel 35 (refer to FIG. 1). The camera 22 has a lens structure configured to generate blur (fade, non-focus image) in an imaging region of an object, such as the driver's face, when the object approaches the camera 22 (projector 21) to be closer than a predetermined distance. Hereafter, a design concept of the lens structure will be described in detail.

Figure 2:
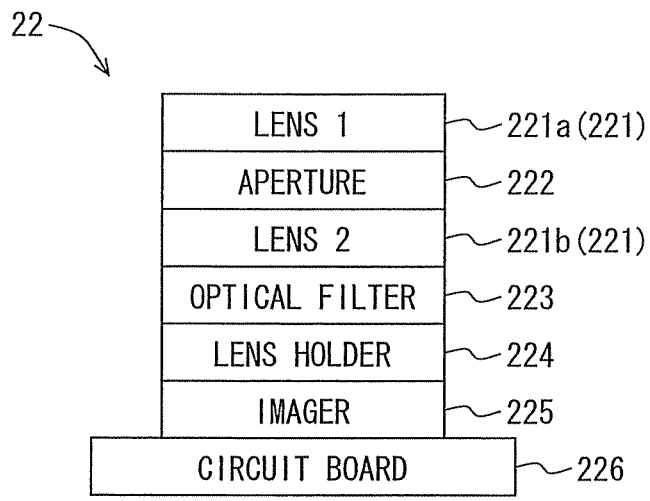
FIG. 2 is a schematic view showing a lens configuration of a camera of the driver monitor system.

FIG. 2 is a sectional view schematically showing the lens structure of the camera 22. As shown in FIG. 2, the lens structure of the camera 22 includes a lens 221, an aperture 222, a visible light cut filter 223, a lens folder 224, an image sensor (imager) 225, a printed circuit board 226, and/or the like. The lens 221 includes multiple lenses. In the present example, the lens 221 includes two lenses 221a and 221b. The aperture 222 is located between the lenses 221a and 221b to control the light volume incident into the camera 22. The visible light cut filter (light filter) 223 cuts off visible light. The lens folder 224 holds the lens 221 and the like. The printed circuit board 226 is mounted with the image sensor 225. The lens structure of FIG. 2 is one example, and the detailed configuration, such as the order of the components, is not limited to that of FIG. 2.

Hereafter, deliberation of the depth of field is made in order to design the lens structure to generate the blur in the imaging region of the object within the specific distance. A hyperfocal distance is defined as a distance at which the infinite distance is barely included in the rear edge of the depth of field when an image object is focused. First, the hyperfocal distance is calculated. The hyperfocal distance H is calculable by the subsequent formula 1 with the focal length f of the lens, the aperture value N of the lens, and the diameter c of the permissible circle of confusion.

$$H = \frac{f^2}{Nc} \quad \text{(formula 1)}$$

Subsequently, the front end at the depth of field and the rear end at the depth of field are calculated when the image object at an arbitrary distance is focused. The front end DN at the depth of field and the rear end DF at the depth of field are calculable respectively by the subsequent formulas 2 and 3 with the distance s of the image object.

$$D_N = \frac{s(H-f)}{H+s-2f} \quad \text{(formula 2)}$$

$$D_F = \frac{s(H-f)}{H-s} \quad \text{(formula 3)}$$

The formulas 1 to 3 represent that: (i) the depth of field becomes deeper, as the focal length of the lens becomes shorter; and (ii) the depth of field becomes deeper, as the aperture is narrowed down to increase the F value. Therefore, contrary to the above-described case, the lens structure may be designed so that the depth of the field becomes narrower, in order to generate blur at a specific distance. Specifically, (1) the aperture value (F value) of the lens may be designed small to open the aperture. In addition or alternatively, (2) the focal length of the lenses may be elongated. Specifically, as for the clause (1), the F value may be set at a value less than or equal to 2. In general, as the F value becomes smaller, it has a desirable view to enable to image a blooming photograph. However, in this case, design of the lens is complicated, and therefore, manufacturing cost for the lens becomes high. Thus, designing the F value to become smaller may not be practical. Nevertheless, it is noted that the image captured with the camera 22 is for the purpose of image processing. In consideration of this, it is unnecessary to prepare a large number of lenses in order to reduce an aberration as much as possible. Thus, the F value can be reduced with relatively low manufacturing cost.

Thus, the lens (focal length) and the aperture are controlled in the above-described way, thereby to control a focus curve. Specifically, by controlling the focus curve, it is enabled to control the form of increasing in blur, according to increase in distance of the image object from a focus range, in which the image object is focused, around the focus range. More specifically, the control of the focus curve enables to control the form of increasing in blur drastically when being out of the focus range and/or the form not to increase in blur largely even when being out of the focus range. In the present embodiment, "proximity to the projector 21" is a case where a user's face approaches the camera 22 (projector 21) at a distance less than or equal to about 20 cm. Therefore, the lens 221 and the aperture 222 (FIG. 2) are designed, so that a blur may occur when the object approaches at a distance less than or equal to about 20 cm.

Figure 14:
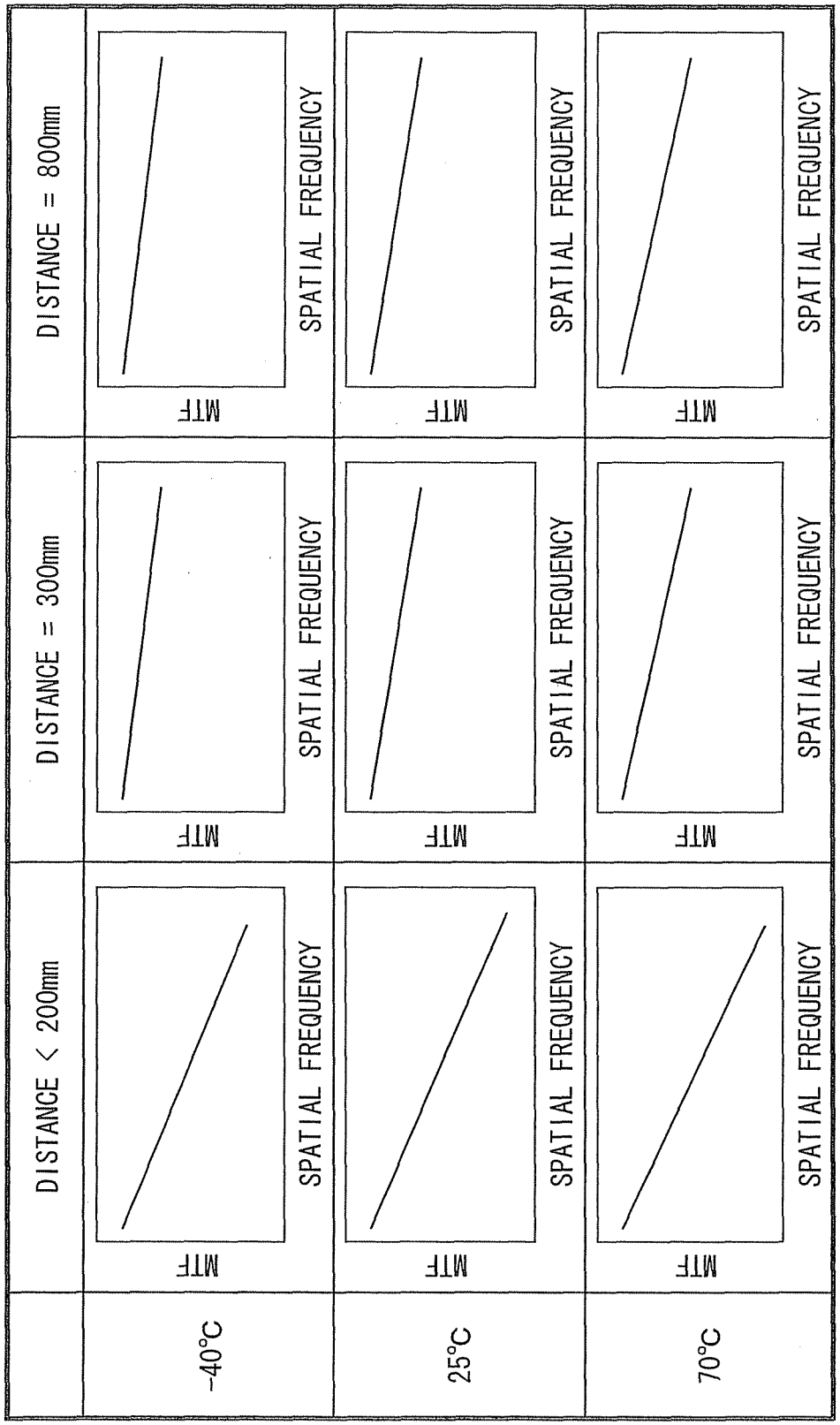
FIG. 14 is an explanatory view showing a relation between an image object distance and a modulation transfer function (MTF).

FIG. 14 is an explanatory view showing a relation between the image object distance and a modulation transfer function (MTF). The MTF is one index representing the degree of the blur of an image and representing the performance of the system (photo acceptance unit) configured to transfer the image signal. When an image causes blur, information on high spatial frequency region in the image is lost. Consequently, the outline of the high spatial frequency region causes blur and becomes unclear.

When the degree of blur is large, the MTF decreases in the corresponding frequency region, and consequently, the transfer property decreases. In consideration of this, dissimilarly to the above-described method, the optical design may be implemented such that the MTF decreases in a specific region in order to design the lens configuration causing blur (fade) in the specific region. As shown in FIG. 14, the MTF (degree of blur) changes with change in temperature. Therefore, the temperature of the lens may be sampled to retrieve temperature information of the lens, and the determination condition whether the driver approaches may be changed according to the retrieved temperature information. In this way, the distance of the object can be detected with sufficient accuracy.

Referring to FIG. 1, the camera 22 is controlled by the imaging control unit 23. The imaging control unit 23 is configured to implement exposure control of the camera 22 to control the gain, the shutter speed, and/of the like, so as to optimally image the driver's face according to the imaging condition. As described above with reference to FIG. 3, the imaging control unit 23 is configured to implement the pulse driving of the shutter of the camera 22, so that the exposure timing of the camera 22 is in a pulse form. The cycle T1 of the pulse includes the driving interval of the shutter and the exposure interval of the shutter. The cycle T1 is set to enable to obtain, for example, 30 frames of photographic image in 1 second. The imaging control unit 23 increases and decreases arbitrarily the exposure time, in which the shutter opens, according to the imaging object.

The photographic image captured by the camera 22 is sent to the image processing unit 25. The image processing unit 25 implements a predetermined image processing on the received photographic image, thereby to detect a face region, which corresponds to the driver's face, from the photographic image. Specifically, the image processing unit 25 stores a characteristic quantity beforehand. The characteristic quantity is, for example, a value reflecting a characteristic of each component of a human's face, such as eyes, a nose, and/or the like. More specifically, the characteristic quantity is shape information, brightness information, and/or the like on each component of a human's face. The image processing unit 25 further implements, for example, a matching processing between the characteristic quantity stored beforehand and the characteristic quantity of a corresponding region in the photographic image. Thereby, the image processing unit 25 detects the face region. It is noted that, the image processing unit 25 may be incapable of detecting the face region, in dependence upon the condition of the photographic image, even through the driver's face is on the photographic image. In addition, the image processing unit 25 is incapable of detecting the face region naturally when the driver's face is not on the photographic image.

The image processing unit 25 is further configured to detect a background region, in addition to the face region. The background region corresponds to structures (vehicle structures) of the vehicle included in the photographic image, such as a pillar, a window frame, a headrest, a sheet, a ceiling, and/or the like. Specifically, the image processing unit 25 stores, for example, a characteristic quantity of a vehicle structure beforehand, similarly to recognition of the face region. The characteristic quantity of a vehicle structure reflects the feature of the vehicle structure, such as the shape information, the brightness information, and/or the like on the vehicle structure. The image processing unit 25 further implements, for example, a matching processing between the characteristic quantity in the background region stored beforehand and the characteristic quantity of a corresponding region in the photographic image. Thereby, the image processing unit 25 detects the background region. It is noted that, the image processing unit 25 is capable of detecting the background region according to the difference between the feature of the background region and the feature of other regions such as the face region and a scenery region. In this case, the image processing unit 25 may not store the characteristic quantity of the background region beforehand. It is further noted that, vehicle structures, such as a sheet and a headrest, are movable according to user's operation. In addition, the steering column, which is mounted with the camera 22 of the present system, is also movable according to user's operation. In consideration of that the relative positions between the camera 22 and vehicle structures in vehicle are variable, the present system may be configured to compensate (correct) the relative positions.

The information on the face region detected by the image processing unit 25 is transmitted to the various systems 107. The various systems 107 may include a system for avoiding drowsy driving and inattentive (face gaze) driving, a system for detecting the eye gaze of the driver, and/or the like. The various systems 107, as needed, detect the driver's face direction, detect the opening of eyes, and/or detect the eye gaze, according to the received information on the face region. Thus, the present system implements a processing for warning and/or the like, as needed.

The projection determination unit 27 is configured to determine whether the driver's face approaches the projector 21. When the projection determination unit 27 determines that the driver's face approaches the projector 21, the projector 21 stops projection of light or dims the light. The processing will be described later. The projection determination unit 27 is configured to receive the photographic image captured by the camera 22 and the recognition result of the image processing unit 25. Each of the processing units 23 to 27 described above is configured as a function of a microcomputer including a CPU, a ROM, a RAM, and/or the like. The CPU executes a control program beforehand stored in the ROM to implement a processing thereby to produce the function of each of the processing units 23 to 27.

The steering angle sensor 28 is for detecting the operation quantity (rotation angle) of the steering wheel 35. The steering angle sensor 28 includes a rotation angle detection sensor, such as a resolver. The projection determination unit 27 is configured to receive the signal representing the operation quantity of the steering wheel 35 detected by the steering angle sensor 28.

Figure 4:
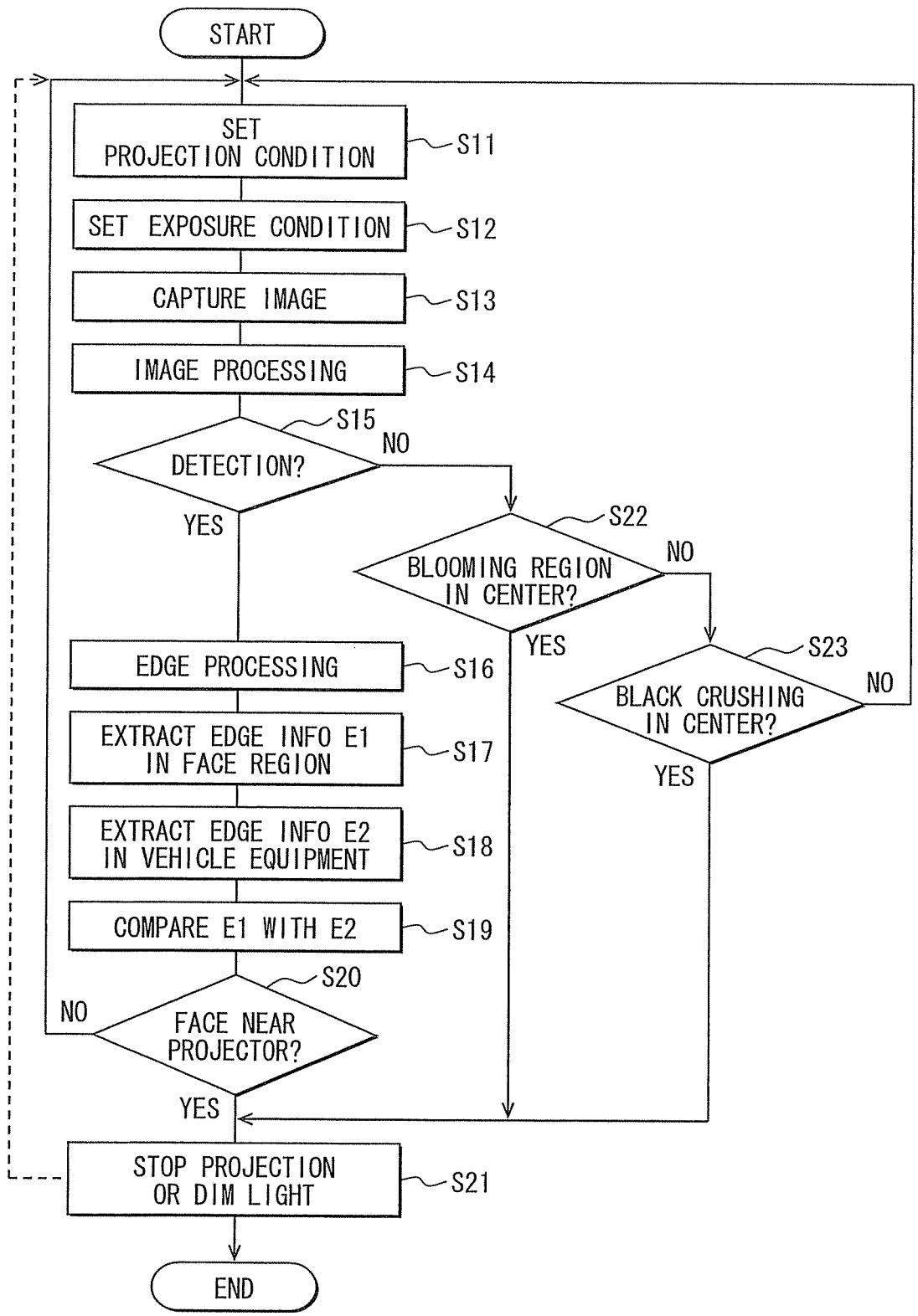
FIG. 4 is a flow chart showing a proximity detection processing according to the first embodiment.

As follows, a proximity detection processing will be described in detail. The proximity detection processing is to determine whether the driver's face approaches the projector 21 and to cause the projector 21 to stop projection of light or to dim the light on determination that the driver's face approaches the projector 21. FIG. 4 is a flow chart showing the proximity detection processing. The proximity detection processing of FIG. 4 is implemented by the driver monitor system 1 as a whole. The proximity detection processing of FIG. 4 is started in response to activation of the driver monitor system 1, specifically, in response to start of the engine of the vehicle. Thereafter, the proximity detection processing is repeatedly implemented at an imaging timing (exposure timing) of the camera 22.

First, the projection control unit 24 sets a light projection condition of projection of light from the projector 21 (S11). The light projection condition may include, for example, the strength of light, the projection timing of light, and/or the like. Specifically, at the first time immediately after activation of the system 1, a default light projection condition is set, and subsequently, the light projection condition is set in consideration of, for example, the previous photographic image of the camera 22 (S11). The projection control unit 24 causes the projector 21 to project light according to the light projection condition being set (S11). Subsequently, the imaging control unit 23 sets the exposure condition of the camera 22, such as the gain, the exposure time, and the exposure timing (S12). Specifically, at the first time immediately after activation of the system 1, a default exposure condition is set, and subsequently, the exposure condition is set in consideration of, for example, the previous photographic image of the camera 22 (S12).

Figure 5A:
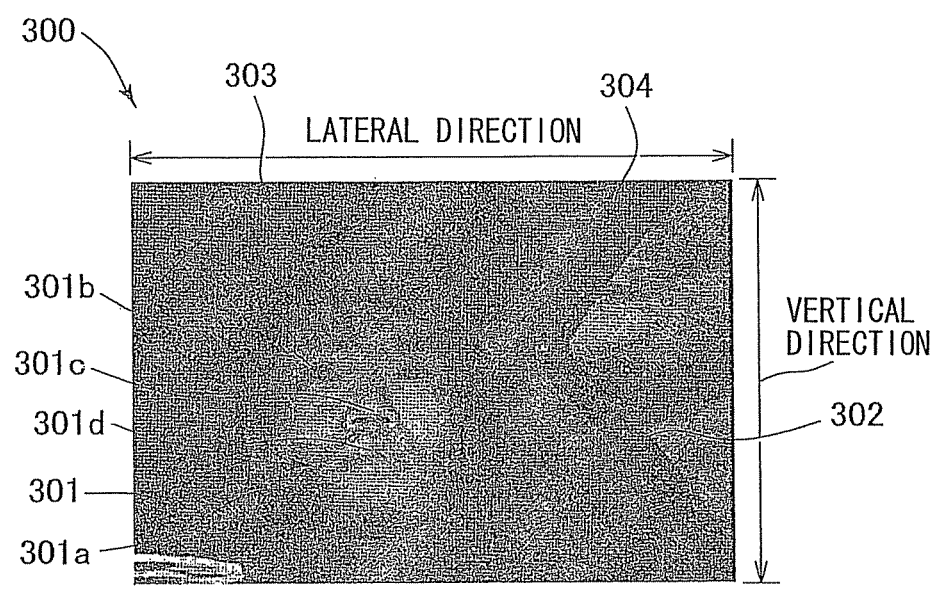
FIG. 5A to FIG. 5D are views showing photographic images captured with the camera.
Figure 5B:
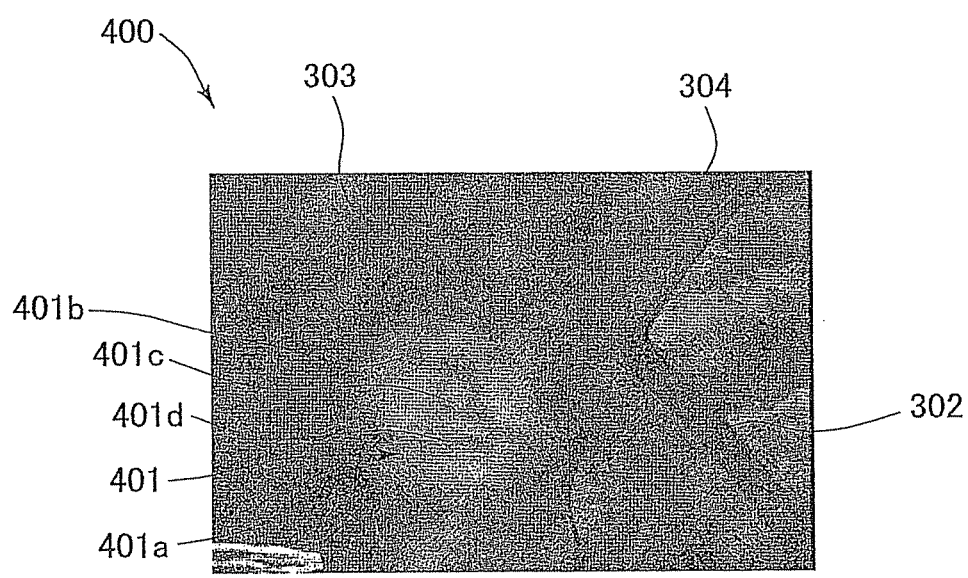
Figure 5C:
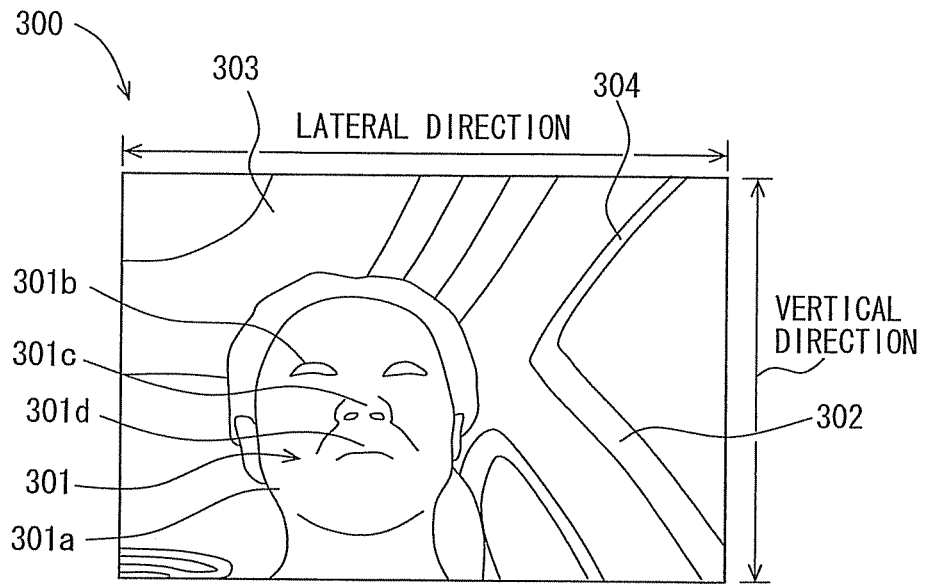
Figure 5D:
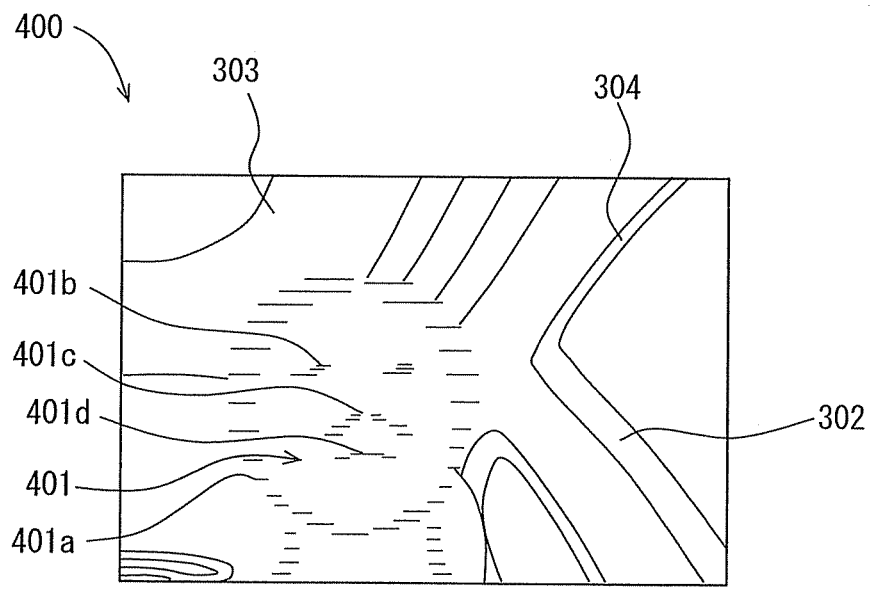

Subsequently, the imaging control unit 23 causes the camera 22 to image the driver's seat peripheral region 10 (S13). FIG. 5A to 5D show an example of the photographic image captured at S13. Specifically, FIG. 5A shows an example of a photographic image 300 when the driver's face does not approach the projector 21. That is, in the condition of FIG. 5A, the driver's face is located at the position P1 distant from the projector 21 (FIG. 1). FIG. 5B shows an example of a photographic image 400 when the driver's face approaches the projector 21. That is, in the condition of FIG. 5B, the driver's face is located at the position P2 close to the projector 21 (FIG. 1). FIG. 5C is a line drawing corresponding to FIG. 5A. FIG. 5D is a line drawing corresponding to FIG. 5B. In FIGS. 5B to 5D, equivalent parts to those in FIG. 5A are denoted by the corresponding same reference numerals.

As shown in FIG. 5A (FIG. 5C), when the driver's face does not approach the projector 21, the photographic image 300 is visually in focus. The photographic image 300 includes a face region 301 corresponding to the driver's face. The face region 301 includes regions respectively corresponding to components of the face. Specifically, the face region 301 includes an outline 301a corresponding to the outline of the driver's face, an eye region 301b corresponding to eyes, a nose region 301c corresponding to a nose, a mouth region 301d corresponding to a mouth, and/or the like. The photographic image 300 further includes background regions corresponding to the vehicle structures. Specifically, the photographic image 300 includes a B-pillar region 302 corresponding to a B pillar of the vehicle, a ceiling region 303 corresponding to the ceiling of the vehicle, a window frame region 304 corresponding to a window frame of the vehicle, and/or the like.

To the contrary, FIG. 5B (FIG. 5D) shows the driver's face approaching the projector 21. In this case, the photographic image 400 includes a face region 401 corresponding to the driver's face. It is noted that a blur occurs in the face region 401 in FIG. 5B (FIG. 5D). The face region 401 includes regions respectively corresponding to components of the face. In the state of FIG. 5B (FIG. 5D), a blur occurs in each of an outline 401a corresponding to the outline of the driver's face, an eye region 401b corresponding to eyes, a nose region 401c corresponding to a nose, a mouth region 401d corresponding to a mouth, and/or the like. That is, the blur weakens the edge sharpness of each region. The photographic image 400 further includes background regions, such as the B-pillar region 302 corresponding to the B pillar of the vehicle, the ceiling region 303 corresponding to the ceiling of the vehicle, the window frame region 304 corresponding to the window frame of the vehicle, and/or the like. The vehicle structures are immovable relative to the projector 21 (camera 22). Therefore, the background regions in FIG. 5B (FIG. 5D) are the same as the background regions in FIG. 5A (FIG. 5C). It is noted that, the optimal exposure conditions for the face differ between FIG. 5A (FIG. 5C) and FIG. 5B (FIG. 5D). Therefore, even though the positions of the background regions do not change, the pixel values differ therebetween.

The camera 22 is equipped with the visible light cut filter 223 (FIG. 2), and therefore, the photographic images 300 and 400 are black-and-white pictures. In the following descriptions, the photographic images 300 and 400 are an object of the proximity detection processing of FIG. 4.

The photographic image captured at S13 is sent to the image processing unit 25. Subsequently, the image processing unit 25 implements a recognition processing to try to detect the face region corresponding to the driver's face in the photographic image or to detect the background region corresponding to the vehicle structure in the photographic image (S14). Specifically, as described above, the image processing unit 25 implements, for example, the matching processing between the characteristic quantity of each component assigned beforehand and the characteristic quantity of each region in the photographic image thereby to try to detect each region. In the example of the photographic images 300 and 400 of FIG. 5A (FIG. 5C) and FIG. 5B (FIG. 5D), the image processing unit 25 implements the recognition processing to detect the face regions 301 and 401, the B-pillar region 302, the ceiling region 303, and the window frame region 304, as the background regions (S14). The recognition result of the recognition processing is sent to the projection determination unit 27. The recognition result may include information on whether the recognition is successful and information on each detected region when the recognition is successful. The photographic image is also sent to the projection determination unit 27, regardless of that the recognition is successful or not.

At S14, the photographic image 300 of FIG. 5A (FIG. 5C) includes the face region 301 without blur. It is noted that, the image processing unit 25 may be incapable of detecting the face region 301 depending on a condition. Specifically, the image processing unit 25 may be incapable of detecting the face region 301 in a case where, for example, the face region 301 is not included in the photographic image 300 previously, and the face region 301 suddenly comes into the photographic image 300. In addition, since the face region 401 of FIG. 5B (FIG. 5D) blurs, it is considered that the face region 401 cannot be detected in general. Nevertheless, in a case where the driver's face approaches the projector 21 at a distance about 20 cm from the projector 21, for example, the degree of the blur of the face region 401 may be still small. In such a case, the image processing unit 25 may be capable of detecting the face region 401. In the following description, it is supposed that the image processing unit 25 is capable of detecting the face regions 301 and 401 from the photographic images 300 and 400 of FIG. 5.

Figure 6A:
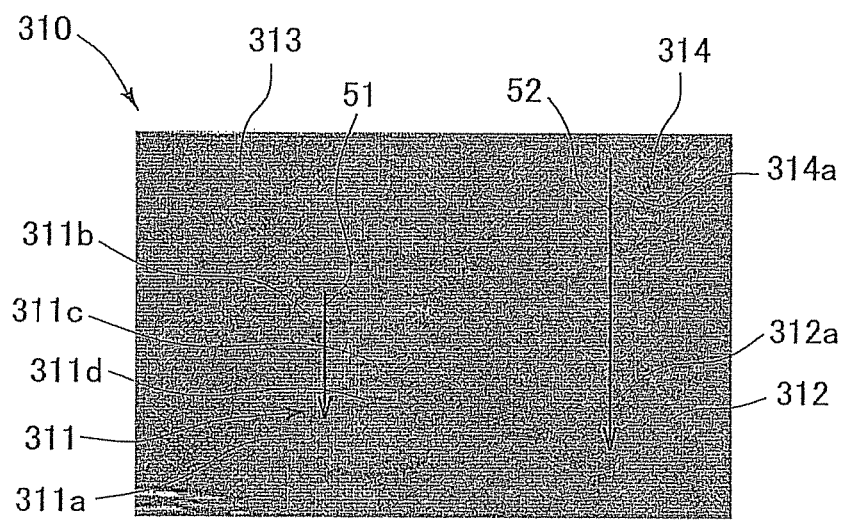
FIG. 6A to FIG. 6D are views showing lateral Sobel images after being implemented with an edge processing.
Figure 6B:
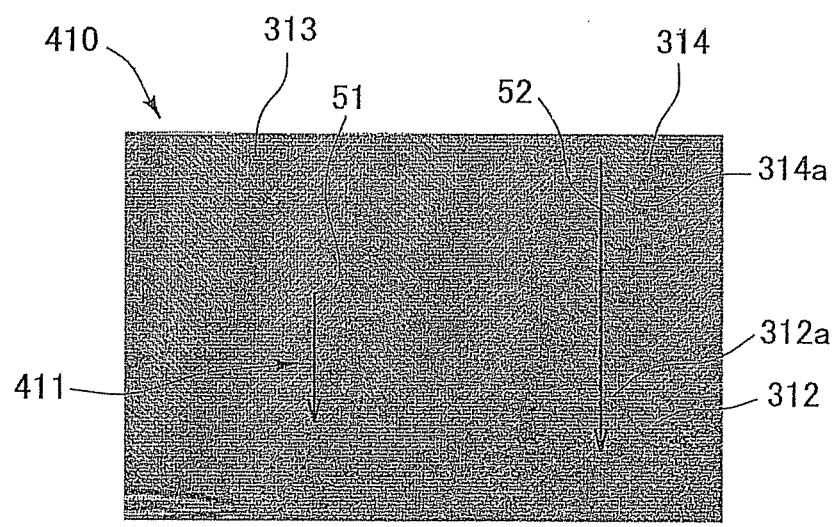
Figure 6C:
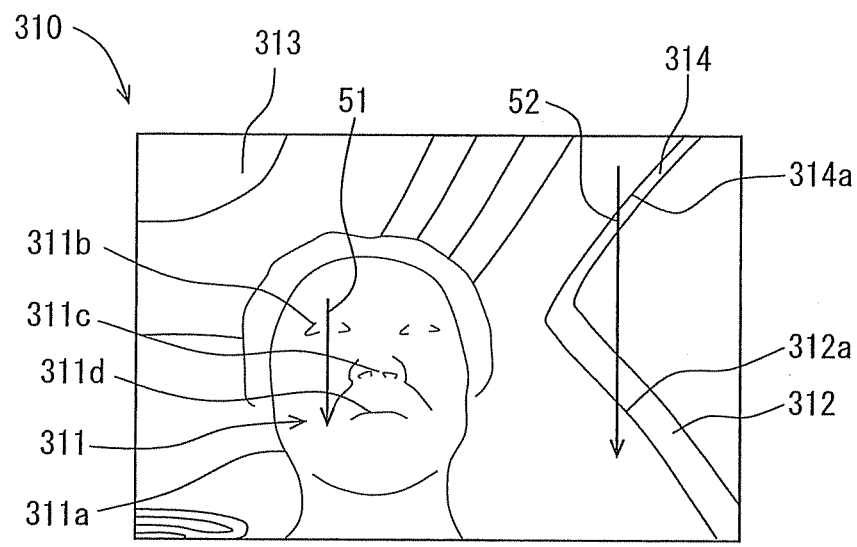
Figure 6D:
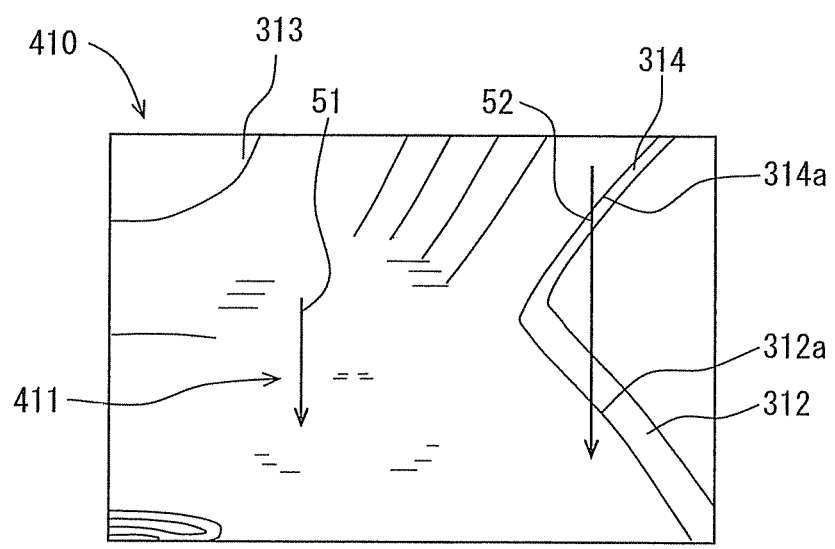

Subsequently, the projection determination unit 27 determines whether the face region is detected from the photographic image according to the recognition result sent from the image processing unit 25 (S15). When the recognition is successful, (S15: Yes) the processing proceeds to S16. At S16, the projection determination unit 27 implements a predetermined edge processing on the photographic image to extract the edge included in the photographic image (S16). Specifically, the edge processing is implemented to filter the photographic image by utilizing the Sobel filter (S16). FIG. 6A shows a Sobel image 310 obtained by filtering the photographic image 300 of FIG. 5A (FIG. 5C) with the Sobel filter. More specifically, the Sobel image 310 of FIG. 6A is a lateral Sobel image obtained by filtering the photographic image 300 of FIG. 5A (FIG. 5C) with the Sobel filter to obtain the edge in the lateral direction. Similarly, FIG. 6B shows a lateral Sobel image 410 obtained by filtering the photographic image 400 in FIG. 5B (FIG. 5D). FIG. 6C is a line drawing corresponding to FIG. 6A. FIG. 6D is a line drawing corresponding to FIG. 6B. In FIGS. 6B to 6D, equivalent parts to those in FIG. 6A are denoted by the same reference numerals.

As shown in FIG. 6A (FIG. 6C) and FIG. 6B (FIG. 6D), in the lateral Sobel images 310 and 410, the edge line corresponding to each edge included in the photographic images 300 and 400 are extracted and emphasized. More specifically, the lateral Sobel image 310 in FIG. 6A (FIG. 6C) includes a region 311 (face region) corresponding to the face region 301 in FIG. 5A (FIG. 5C). The face region 311 includes edges corresponding to the regions in FIG. 5A (FIG. 5C). Specifically, the face region 311 includes an edge 311a corresponding to the outline 301a of the face region 301, an edge 311b corresponding to the eye region 301b, an edge 311c corresponding to the nose region 301c, and an edge 311d corresponding to the mouth region 301d. The lateral Sobel image 310 further includes regions corresponding to the background regions in FIG. 5A (FIG. 5C). Specifically, the lateral Sobel image 310 includes a region 312 corresponding to the B-pillar region 302, a region 313 corresponding to the ceiling region 303, and a region 314 corresponding to the window frame region 304. In addition, in FIG. 6A (FIG. 6C), the B-pillar region 312 includes an edge 312a of the B-pillar, and the window frame region 314 includes an edge 314a of the window frame.

To the contrary, the lateral Sobel image 410 in FIG. 6B (FIG. 6D) includes a region 411 corresponding to the face region 401 in FIG. 5B (FIG. 5D). Nevertheless, the face region 411 can hardly be detected in FIG. 6B (FIG. 6D). That is, the edge sharpness of the face region 411 is weakened compared with the edge sharpness of the face region 311 in FIG. 6A (FIG. 6C). The lateral Sobel image 410 further includes background regions, such as the B-pillar region 312 corresponding to the B pillar of the vehicle, the ceiling region 313 corresponding to the ceiling of the vehicle, the window frame region 314 corresponding to the window frame of the vehicle, and/or the like. The background regions in FIG. 6B (FIG. 6D) are the same as the background regions in FIG. 6A (FIG. 6C). It is noted that at S16, the photographic image may be filtered with a Sobel filter to detect the edge of the photographic image in the vertical direction, and/or the photographic image may be filtered with a Sobel filter to detect the edge in an oblique direction, in addition to or alternative to the lateral Sobel image. In this way, Sobel images with edges extracted in various directions may be obtained.

Subsequently, the projection determination unit 27 extracts edge information E1 from the Sobel image (S17). The edge information E1 reflects the feature of the edge of the face region in the region of the Sobel image obtained at S16. At S17, instead of the face region detected by the image processing unit 25, a region (unfixed region) other than known background regions may be set as a face region. In the cases of the lateral Sobel images 310 and 410 in FIG. 6A (FIG. 6C) and FIG. 6B (FIG. 6D), the edge information E1 on regions (face regions 311 and 411) other than the background regions including the B-pillar region 312, the ceiling region 313, and the window frame region 314 is extracted.

Figure 7A:
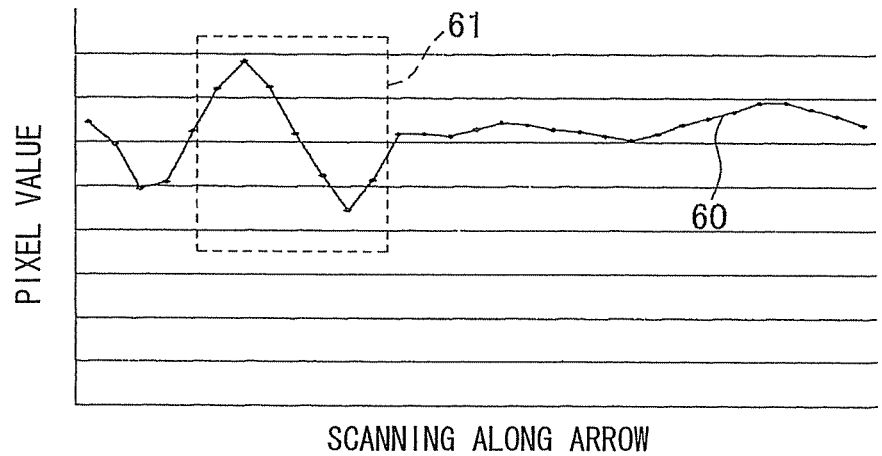
FIG. 7A to FIG. 7C are graphs each showing a brightness change being edge information.
Figure 7B:
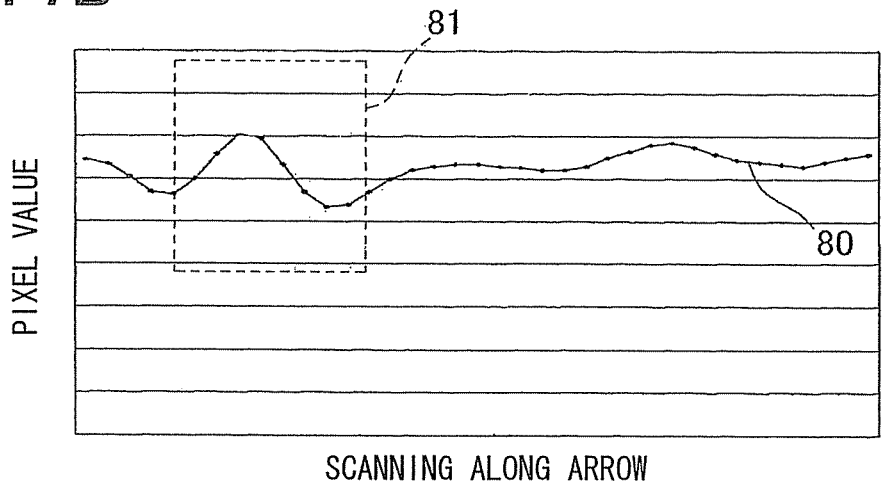

More specifically, the edge information E1 representing the brightness change in the face region is extracted (S17). In the lateral Sobel images 310 and 410 of FIG. 6A (FIG. 6C) and FIG. 6B (FIG. 6D), the edge in the lateral direction is emphasized. Therefore, in this case, the brightness change between the pixels arranged in the vertical direction is extracted. FIG. 7A shows a line 60 representing the change in the pixel value along an arrow 51 in FIG. 6A (FIG. 6C). The line 60 is equivalent to the edge information E1 in the face region. FIG. 7B shows a line 80 (edge information E1) representing the change in the pixel value along the arrow 51 in FIG. 6B (FIG. 6D). The arrow 51 in FIG. 6B (FIG. 6D) is drawn at the same position as the position of the arrow 51 in FIG. 6A (FIG. 6C).

As shown in FIG. 7A, the brightness change represented by the line 60 largely varies in a region 61 in FIG. 7A. More specifically, the amplitude of the line 60, which is the difference between the maximum pixel value and the minimum pixel value, is large in the region 61 (edge peripheral), and the Inclination of the line 60 is also large in the region 61. The tendency of the line 60 appears in this way, since the pixel value in the region 61 corresponds to the pixel value in the edge 311b of the eye region in FIG. 6A (FIG. 6C). The amplitude and the inclination of the line 60 reflect the feature (edge sharpness) of the edge in the face region 311. To the contrary, though the line 80 in FIG. 7B changes in a region 81, which corresponds to the edge of the eye region, nevertheless, the amplitude and the inclination of the line 80, i.e., the change in the line 80 is smaller that those of the line 60 in FIG. 7A. The tendency of the line 80 appears in this way, since the edge sharpness in the face region 411 is weakened.

In the above description, the brightness change E1 along the arrow 51 in FIG. 6A (FIG. 6C) and FIG. 6B (FIG. 6D) is exemplified. It is noted that, at S17, the brightness change E1 in the pixel value may be extracted in all the face region. In the above description, the brightness change E1 in the face regions 311 and 411 of the lateral Sobel images 310 and 410 is exemplified. It is noted that, at S17, the brightness change E1 in the face region may be extracted from Sobel images in various directions such as a vertical Sobel image and an oblique Sobel image. In this case, the brightness change E1 in a direction perpendicular to the filtering direction of the Sobel filter may be extracted. Specifically, for example, the brightness change E1 along the lateral direction may be extracted from the vertical Sobel image.

Figure 7C:
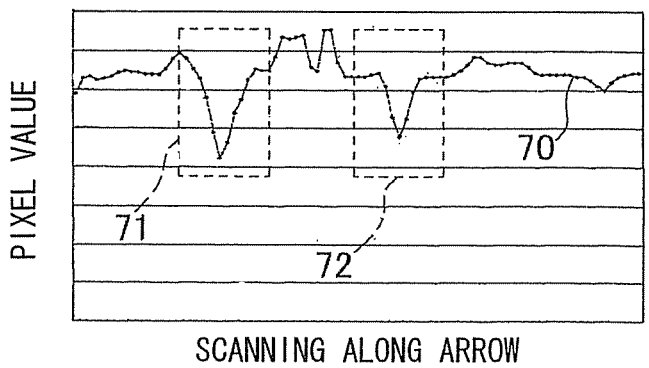

Subsequently, the projection determination unit 27 extracts edge information E2 from the Sobel image (S18). The edge information E2 reflects the feature of the edge of the background region in the region of the Sobel image obtained at S16. Specifically, the brightness change in the background region is extracted as the edge information E2, similarly to the edge information E1 in the face region extracted at S17, as described above. The method for extraction of the edge information E2 is the same as the method described at S17. FIG. 7C shows a line 70 representing the change in the pixel value along an arrow 52 in FIG. 6A (FIG. 6C) and FIG. 6B (FIG. 6D). The line 70 is equivalent to the edge information E2 in the background region. The arrow 52 extends in the lateral Sobel images 310 and 410 to go through the edge 314a in the window frame region 314 and the edge 312a in the B-pillar region 312. Therefore, the line 70 changes largely around the edges 314a and 312a. Specifically, in FIG. 7C, the amplitude and the inclination of the line 70 change largely in a region 71, which corresponds to the edge 314a in the window frame region 314, and a region 72, which corresponds to the edge 312a in the B-pillar region 312. The amplitude and the inclination of the line 70 reflect the feature (edge sharpness) of the edge in the background region including the window frame region 314 and the B-pillar region 312.

Similarly to S17, at S18, the brightness change E2 in all the known background region may be extracted. In addition, the brightness change E2 in the background region may be extracted from each of the Sobel images in various directions.

Subsequently, in order to determine whether the edge information E1 (brightness change) in the face region extracted at S17 is the edge information with blur, the projection determination unit 27 compares the extracted edge information E1 with the edge information E2 in the background region without blur (S19). Specifically, the projection determination unit 27 normalizes the edge information E1 in the face region with the edge information E2 in the background region (S19). That is, the projection determination unit 27 calculates edge information E0 in the face region on the basis of the edge information E2 without blur, as a reference (S19). For example, the value of the edge information E0 after being normalized is represented in a range 0 to 1. In addition, as the value is closer to 1, the edge information E1 and E2 further resemble to each other. On the present premise, in the example shown by FIG. 6A (FIG. 6C), the face region 311 does not blur, and therefore, the edge information E0 in face region 311 after being normalized is represented by a value about 1. To the contrary, in the example shown by FIG. 6B (FIG. 6D), the face region 411 blurs, and therefore, the edge information E0 in the face region 411 after being normalized is represented by a value much less than 1.

Subsequently, the projection determination unit 27 determines whether the edge information E0 after being normalized is less than a predetermined threshold Eth. Thereby, the projection determination unit 27 determines whether the driver's face approaches the projector 21 (S20). The threshold Eth is set at a boundary value between the edge information E0 with blur and the edge information E0 without blur. When the projection determination unit 27 determines that the edge information E0 is greater than or equal to the threshold Eth (S20: No), the projection determination unit 27 determines that the edge information E0 is edge information without blur. That is, in this case, the projection determination unit 27 determines that the driver's face does not approach the projector 21. Thus, the processing returns to S11. In this case, the light strength is maintained at the normal condition, and the subsequent light projection condition is set at S11. That is, in the case of FIG. 6A (FIG. 6C), the projection determination unit 27 determines that the edge information E0 is greater than or equal to the threshold Eth (S20: No). Thus, the light strength is maintained at the normal condition.

To the contrary, when the edge information E0 is less than the threshold Eth (S20: Yes), the processing proceeds to S21. In this case, the projection control unit 24 determines that the edge information E0 is edge information with blur. Thus, the projection control unit 24 determines that the driver's face approaches the projector 21 and causes the projector 21 to stop or dim projection of light (S21). When causing the projector 21 to dim projection of light, the projection control unit 24 reduces the light strength by a predetermined rate (for example, 80% OFF) from a normal strength when the face does not approach the projector 21. In the case of FIG. 6B (FIG. 6D), the projection determination unit 27 determines that the edge information E0 is less than the threshold Eth (S20: Yes). Thus, the projector 21 is caused to stop or dim projection of light (S21). With the present configuration, eye-strain of the driver can be mitigated. Thus, processing of the flow chart in FIG. 4 is terminated. In this case, the processing of FIG. 4 may be, for example, resumed after a predetermined time period elapses.

It is conceived that, when an object, such as the driver's face, approaches the camera 22 rapidly, the photographic image of the camera 22 may not cause blur therein. In this case, the projector 21 may project light strongly to the object, which approaches the camera 22 rapidly, and the object may reflect the strong projected light. Consequently, the camera 22 generates a photographic image with the light reflected strongly. Therefore, the image around the center of the photographic image corresponding to the imaging region of the object becomes significantly whity unclear image in a blooming unclear photo state (blooming region). When the object further approaches the camera 22, the camera 22 is almost covered with the object. Therefore, the image around the center of the photographic image becomes significantly blackish unclear image in a black crushing photo state (black crushing). In these cases, the projector 21 may be caused to stop or dim projection of light. At S15, when the image processing unit 25 cannot detect the face region from the photographic image (S15: No), the processing proceeds to S22.

At S22, the projection determination unit 27 determines whether a blooming photo is detected (S22) entirely around the center of the photographic image obtained at S13. Specifically, at S22, the projection determination unit 27 determines whether the pixel values are saturated entirely around a predetermined area in the center of the photographic image. More specifically, in a case where each of the pixel values is represented with, for example, 256 gradation levels, the projection determination unit 27 determines whether the pixel values are about, for example, 256 and saturated entirely around the predetermined area. A detection target of the blooming photo may be set at any size in the predetermined area around the center region. When the camera 22 is in a high dynamic range mode (HDR mode), the blooming photo may hard to occur. In consideration of this, at S22, the projection determination unit 27 may determine whether substantially all the pixel values in the predetermined area around the center of the photographic image become greater than or equal to a predetermined threshold (S22). The predetermined threshold is equivalent to the first threshold representing that the pixel value is enough to cause the blooming photo.

When all or substantially all the pixel values in the predetermined area around the center of the photographic image are saturated (S22: Yes), the projection determination unit 27 determines that the blooming photo is detected. That is, the projection determination unit 27 determines that an object, such as the driver's face, approaches the projector 21 (camera 22) rapidly. In response to the determination, the projection determination unit 27 causes the projector 21 to stop or dim projection of light (S21). To the contrary, when the projection determination unit 27 determines that the blooming photo is not detected (S22: No), the processing proceeds to S23.

At S23, the projection determination unit 27 determines whether a black crushing photo is detected (S23) entirely around the center of the photographic image obtained at S13. Specifically, at S23, the projection determination unit 27 determines whether the pixel values are about 0 entirely around a predetermined area in the center of the photographic image. It is noted that, the predetermined area around the center of the photographic image at S22 and the predetermined area around the center of the photographic image at S23 may be coincide with each other or may be different from each other. Actually, even in the black crushing photo, the pixel values are not necessarily 0 and may be small values due to thermal noise or due to black level correction caused by the image sensor. In addition, when the camera 22 has a high sensitivity, the black crushing photo may hardly occur. In consideration of this, at S23, the projection determination unit 27 may determine whether substantially all the pixel values in the predetermined area around the center of the photographic image become less than a predetermined threshold (S23). The predetermined threshold is equivalent to the second threshold representing that the pixel value is enough to cause the black crushing photo.

When all or substantially all the pixel values in the predetermined area around the center of the photographic image are about 0 (S23: Yes), the projection determination unit 27 determines that the black crushing photo is detected. That is, the projection determination unit 27 determines that an object, such as the driver's face, approaches the projector 21 (camera 22) rapidly. In response to the determination, the projection determination unit 27 causes the projector 21 to stop or dim projection of light (S21). To the contrary, when the projection determination unit 27 determines that the black crushing photo is not detected (S23: No), the processing returns to S11. In this case, the light strength is maintained at the normal condition, and the subsequent light projection condition is set at S11.

As described above, in the present embodiment, it is determined whether blur occurs in the photographic image thereby to determine whether the driver's face approaches. With the present configuration, proximity of the driver's face can be correctly detected. In addition, the edge information E0 in the face region is calculated with reference to the edge information E2 as a reference in the background region without blur. Therefore, determination whether the edge information E0 is edge information with blur can be made correctly. In addition, it is determined that an object such as the driver's face approaches when the blooming photo and/or the black crushing photo occur in the photographic image. Therefore, even in the case where the driver's face approaches projector 21 rapidly not to cause blur in the photographic image, the projection is enabled to stop or dim projection of light.

The equipments in the interior of the vehicle includes components located out of the range of the depth of field, and such components causes blur regularly. It is meaningless to implement the comparison with reference to such components causing blur regularly. Therefore, such components causing blur regularly is excluded. With the present configuration, the edge information of the known equipments, which are located in the range of the depth of field, is utilized.

Second Embodiment

Figure 8:
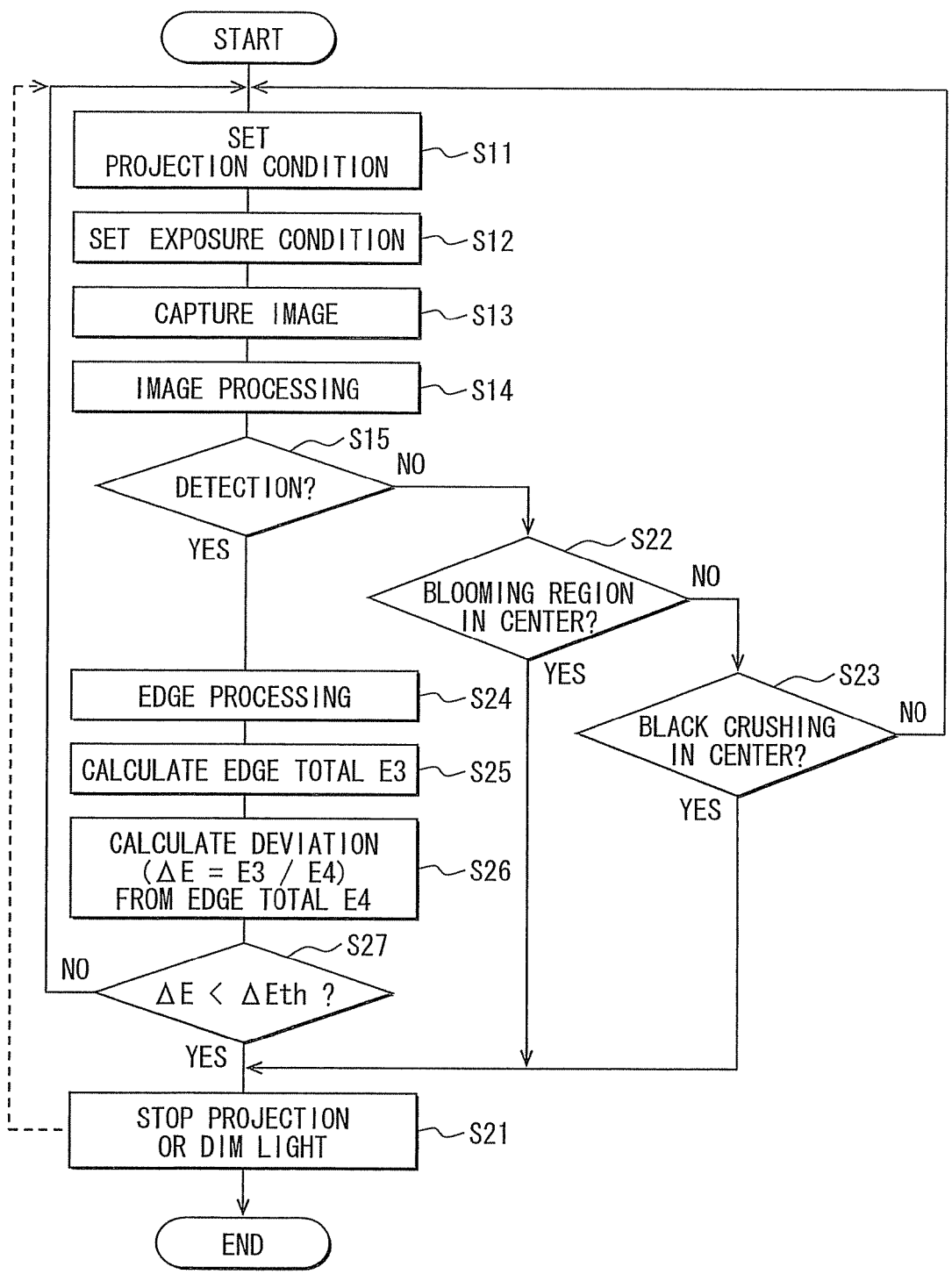
FIG. 8 is a flow chart showing a proximity detection processing according to the second embodiment.

Subsequently, the face imaging system according to the second embodiment will be described. As follows, difference of the face imaging system from the first embodiment will be mainly described. The configuration of the driver monitor system of the present embodiment is substantially the same as the driver monitor system 1 of FIG. 1. In the present embodiment, the method, which is for determination whether blur occurs in the photographic image in the proximity detection processing to determine whether the driver's face approaches the projector 21, is different from that of the first embodiment. As follows, the proximity detection processing according to the present embodiment will be described. FIG. 8 is a flow chart showing the proximity detection processing according to the present embodiment. In FIG. 8, steps equivalent to those of the proximity detection processing in FIG. 4 are denoted by the same reference numerals. The difference of the proximity detection processing in FIG. 8 from the proximity detection processing in FIG. 4 is to implement processing S24 to S27, instead of the processing S16 to S20 in FIG. 4.

Figure 9A:
FIG. 9A and FIG. 9B are views each showing an edge-binarized image being implemented with an edge processing.

At S15, when the image processing unit 25 successfully detects the face region from the photographic image (S15: Yes), the processing proceeds to S24. At S24, the projection determination unit 27 implements a predetermined edge processing on the photographic image obtained at S13 to extract the edge included in the photographic image (S24). The edge processing at S24 differs from the edge processing at S16 in the first embodiment. Specifically, an edge binarization processing is implemented (S24) as the edge processing. In the edge binarization processing, an edge greater than or equal to a predetermined strength is assigned with the pixel value of 1, and an edge less than the predetermined strength is assigned with the pixel value of 0. FIG. 9A shows an edge-binarized image 320 produced by implementing the edge binarization processing on the photographic image 300 in FIG. 5A (FIG. 5C) showing the driver's face, which does not approach the projector 21, without blur. As shown in FIG. 9A, the edge-binarized image 320 includes a region 321 corresponding to the face region 301 in FIG. 5A (FIG. 5C). The face region 321 includes edges greater than the predetermined strength. Specifically, the face region 321 includes an edge 321a corresponding to the outline 301a of the face region 301, an edge 321b corresponding to the eye region 301b, an edge 321c corresponding to the nose region 301c, and an edge 321d corresponding to the mouth region 301d. The edge-binarized image 320 further includes an edge in the background region, such as an edge 322 of the B-pillar. In the following description, the edge-binarized image 320 in FIG. 9A is an object of processing in FIG. 8.

Subsequently, the projection determination unit 27 calculates a total of edge E3 (edge information) included in the face region of the edge-binarized image (S25). Specifically, the projection determination unit 27 counts the number of pixels assigned with the pixel value of 1 (S25). In the processing of S25, a region (unfixed region) other than the known background region may be set as the face region In the case of FIG. 9A, the total of edge E3 including the edge 321a to 321d in face region 321 is calculated.

Subsequently, a change rate ΔE (=E3/E4) is calculated (S26). The change quantity ΔE represents a rate (quantity) by which a total of edge E4, when the driver's face does not approach the projector 21, is changed to the total of edge E3 calculated at S25. The total of edge E4 used as a reference for the change rate ΔE is, for example, the total of edge E3 calculated at S25 when it is determined that the driver's face does not to approach in the previous processing of FIG. 8. In the case of FIG. 9A, the edge-binarized image 320 shows the state when the driver's face does not approach. Therefore, the total of edge E3 does not largely change from the reference total E4. Therefore, the change rate ΔE is a value about 1.

Subsequently, the projection determination unit 27 determines whether the change rate ΔE calculated at S26 is less than a predetermined threshold ΔEth (S27). The threshold ΔEth is a boundary value between the change rate ΔE when blur occurs and the change rate ΔE when blur does not occur. When the projection determination unit 27 determines that the change rate ΔE is greater than or equal to the threshold ΔEth (S27: No), the projection determination unit 27 determines that blur does not occur in the face region. That is, in this case, the projection determination unit 27 determines that the driver's face does not approach the projector 21. Thus, the processing returns to S11. In this case, the light strength is maintained at the normal condition, and the subsequent light projection condition is set at S11. In the case of FIG. 9A, the projection determination unit 27 determines that the change rate ΔE is greater than or equal to the threshold ΔEth (S27: No). Thus, the light strength is maintained at the normal condition.

To the contrary, when the change rate ΔE is less than the threshold ΔEth (S27: Yes), the processing proceeds to S21. In this case, the projection control unit 24 determines that blur occurs in the face region. Thus, the projection control unit 24 determines that the driver's face approaches the projector 21 and causes the projector 21 to stop or dim projection of light (S21). Thus, processing of the flow chart in FIG. 8 is terminated. In this case, the processing of FIG. 8 may be, for example, resumed after a predetermined time period elapses. Other processings are equivalent to those of FIG. 4, and description thereof is omitted.

Figure 9B:
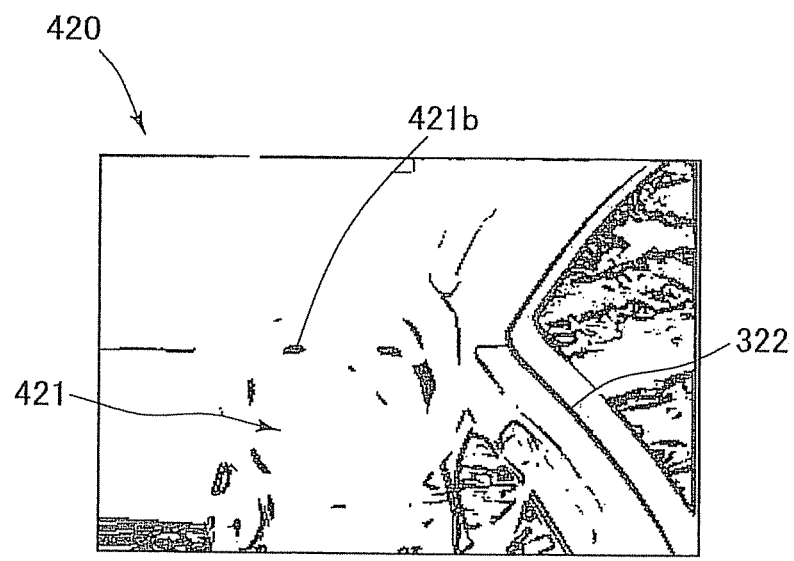

In the above description, the processing of FIG. 8 when the driver's face does not approach the projector 21 has been described with reference to FIG. 9A. As follows, the processing of FIG. 8 in the case of the photographic image 400 shown in FIG. 5B (FIG. 5D) when the driver's face approaches the projector 21 will be described. When the image processing unit 25 detects successfully the face region 401 in the photographic image 400 (S15: Yes), the edge binarization processing is subsequently implemented on the photographic image 400 (S24). FIG. 9B shows an edge-binarized image 420 obtained by the edge binarization processing. In FIG. 9B, equivalent parts to those in FIG. 9A are denoted by the same reference numerals. As shown in FIG. 9B, the edge-binarized image 420 includes the face region 421. Nevertheless, edge of each component of the face does not appear in the face region 421, except for an edge 421b partially in the eye region 401b (refer to FIG. 5B (FIG. 5D)). The present tendency appears, since blur occurs in the face region 401 of the original photographic image 400, and therefore, the edge sharpness in the face region 401 is weakened.

Subsequently, the total of edge E3 included in the face region 421 of the edge-binarized image 420 is calculated (S25). In this case, the calculated total of edge E3 is largely reduced from the total of edge E3 in the face region 321 in FIG. 9A described above. Subsequently, the change rate ΔE of the present total of edge E3 relative to the total of edge E4 being the reference is calculated (S26). The total of edge E4 being the reference is, for example, the total of edge E3 in the face region 321 in FIG. 9A. In this case, the change rate ΔE is a value much less than 1. Therefore, at subsequent S27, it is determined that the change rate ΔE is less than the threshold ΔEth (S27: Yes). Thus, on determination that the driver's face approaches the projector 21, the projector 21 is caused to stop or dim projection of light (S21).

As described above, in the present embodiment, the total of edge in the present photographic image is determined with reference to the total of edge in the photographic image without blur when the driver's face does not approach the projector 21. Therefore, it can be determined correctly whether blur occurs in the present photographic image.

(First Modification)

In the embodiment, it is determined whether the driver's face approaches the projector 21 according to whether blur occurs in the photographic image. It is noted that, the determination method whether blur occurs in the photographic image is not limited to the method of the embodiment. Various generally-known methods, such as the method disclosed in publication of Japanese patent No. 449316, may be employed as the determination method. In the second embodiment, it is determined whether blur occurs in the face region according to the change rate ΔE in the total of edge in the face region. It is noted that the determination may be made according to the change in the total of edge in the entire photographic image. In this case, the total of edge and the change rate of the total of edge may be calculated in the background region, in addition to the face region. When blur occurs in the photographic image, the total of edge anyhow reduces compared with the case where blur does not occur. Therefore, it can be determined whether blur occurs in the photographic image also according to the total of edge in the entire photographic image. With the present configuration, it is not necessary to distinguish the face region from the background region. Therefore, the algorithm of calculation can be simplified.

In the above embodiments, it is determined whether the edge in the present face region is caused by blur, according to the comparison with the reference edge in the region without blur. Specifically, the reference is the edge in the background region in the first embodiment, and the reference is the edge in the previous face region in the second embodiment. The determination of the edge is not limited to those in the above embodiments and may be made according to only the feature of edge (edge sharpness) in the present face region. In this case, a threshold of the edge sharpness for determination whether blur occurs is determined beforehand. Further, comparison between the edge sharpness and the threshold is made in the present face region thereby to determine whether blur occurs in the present face region. In this way, blur is determined only by the edge sharpness in the present face region, and therefore, the algorithm of calculation can be simplified.

(Second Modification)

In the first and second embodiments, when the image processing unit 25 successfully detects the face region, (S15: Yes in FIG. 4 and FIG. 8), determination whether the face approaches the projector 21 is made according to whether blur occurs in the photographic image. It is noted that, even when the image processing unit 25 cannot detect the face region, proximity of the face may be determined according to blur in the photographic image. In this case, the unfixed region other than the known background region is set as the face region, and blur in the face region is determined. For example, at S15 in FIG. 4 and FIG. 8, when the face region is not successfully detected (S15: No), the same processing as that of S16 to S20 in FIG. 4 or S24 to S27 in FIG. 8 is implemented in advance of the processing of S22 and S23 or subsequent to the processing of S22 and S23. Thus, determination whether blur occurs in the photographic image is made. The method for determining blur in the photographic image in this way has a merit to enable determination of proximity of a face regardless of recognition of the face region.

(Third Modification)

Figure 10:
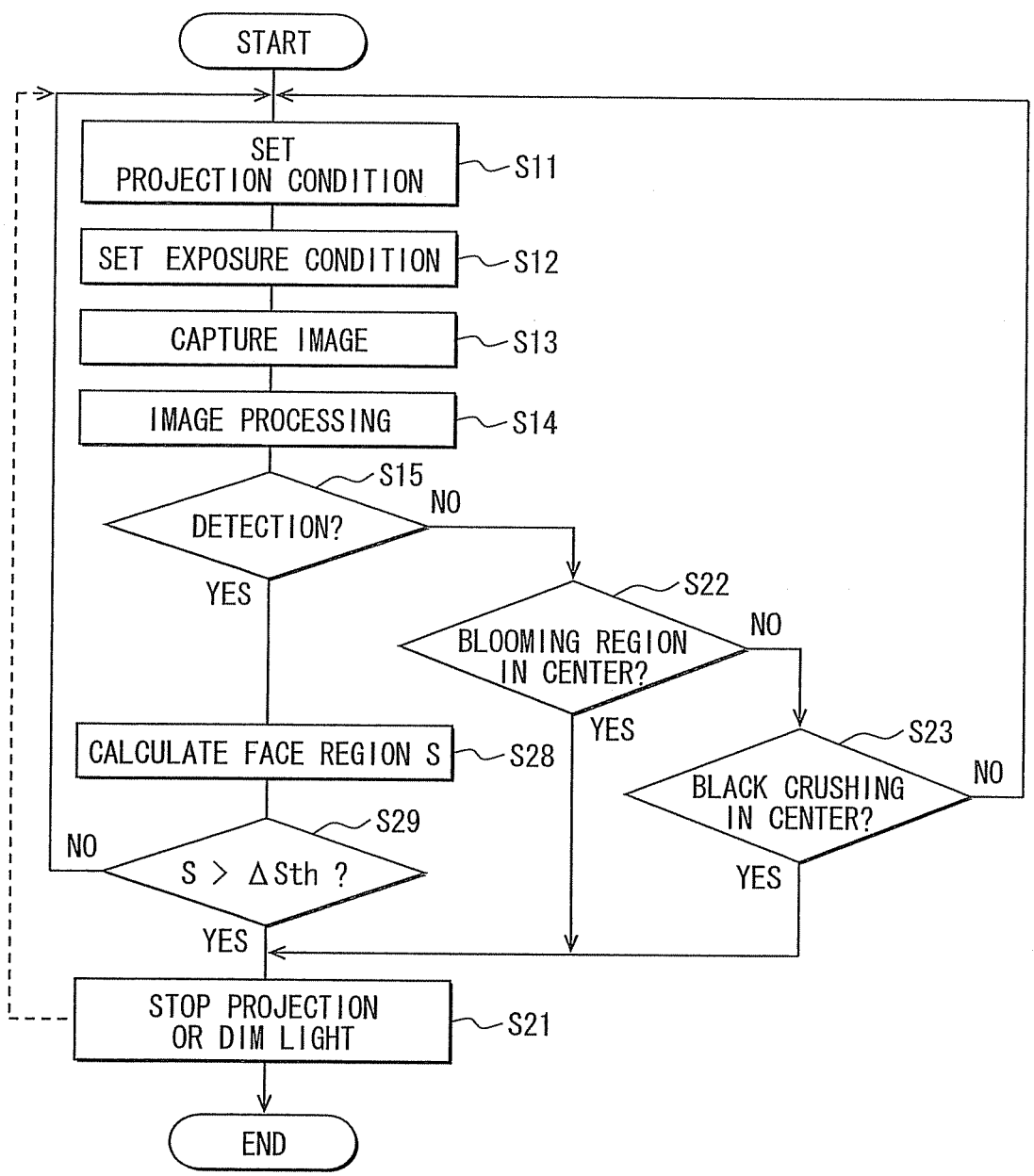
FIG. 10 is a flow chart showing a proximity detection processing according to the third modification.

The projector 21 and the camera 22 are located on the upper surface of the steering column at positions close to each other. Therefore, when the driver's face approaches the projector 21, the driver's face approaches simultaneously approaches the camera 22. Therefore, as the driver's face approaches the projector 21, the size of the face region becomes larger relative to the photographic image. That is, the occupation rate of the face region relative to the photographic image becomes larger. In consideration of this, when the image processing unit 25 successfully detects the face region, a method for determining proximity of a face according to the size of the detected face region may be employed, in replace of the method of determination according to blur in the photographic image. Specifically, for example, the processing of the flow chart shown in FIG. 10 is implemented. In FIG. 10, steps equivalent to those of the proximity detection processing in FIG. 4 and FIG. 8 are denoted by the same reference numerals. The difference of the proximity detection processing in FIG. 10 from the proximity detection processings in FIG. 4 and FIG. 8 is to implement processing S28, S29, instead of the processing S16 to S20 in FIG. 4 or instead of the processing S24 to S27 in FIG. 8.

In FIG. 10, when the image processing unit 25 successfully detects the face region, (S15: Yes), the projection determination unit 27 calculates the size S of the face region being detected (S28). Subsequently, the projection determination unit 27 determines whether the size S of the face region is greater than a predetermined threshold Sth (S29). The threshold Sth may be set at a size of the face region when, for example, the distance from the projector 21 is about 20 cm. For example, in the case of FIG. 5A (FIG. 5C) and FIG. 5B (FIG. 5D), the size of the face region 301 and 401 respectively relative to the photographic images 300 and 400 is determined.

At S29, when the size S of the face region is less than the threshold Sth (S29: No), the projection determination unit 27 determines that the driver's face does not approach the projector 21, and the processing returns to S11. In this case, the light strength is maintained at the normal condition, and the subsequent light projection condition is set at S11. To the contrary, when the size S of the face region is greater than the threshold Sth (S29: Yes), the projection determination unit 27 determines that the driver's face approaches the projector 21. In this case, the projector 21 is caused to stop or dim projection of light (S21). Thus, processing of the flow chart in FIG. 10 is terminated. In this case, the processing of FIG. 10 may be, for example, resumed after a predetermined time period elapses. Other processings are equivalent to those of FIG. 4 and FIG. 8, and description thereof is omitted.

Third Embodiment

Subsequently, the face imaging system according to the third embodiment will be described. As follows, difference of the face imaging system from the above embodiments will be mainly described. In the case where the face imaging system is employed in a vehicle, the camera may be concealed with an obstacle, such as an arm of a driver, when the driver performs steering operation in driving of the vehicle. That is, steering concealment may occur in driving of the vehicle. When the steering concealment occurs, the camera cannot image the driver's face. Therefore, in the case of steering concealment, it may be wasteful to continue causing the camera to image and/or to continue to cause the projector to project light. The present third embodiment is to reduce such waste, when steering concealment occurs.

Figure 11:
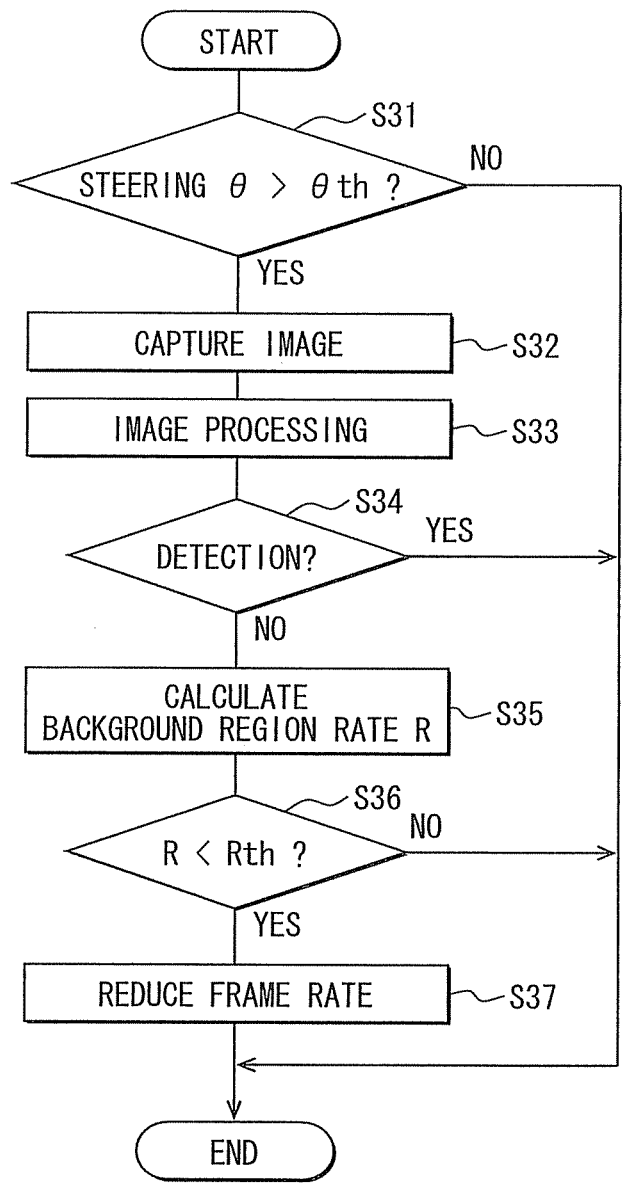
FIG. 11 is a flow chart showing a steering concealment detection processing according to the third embodiment.

The configuration of the driver monitor system of the present embodiment is substantially the same as the driver monitor system 1 of FIG. 1. In addition to the proximity detection processings of the first and second embodiments (refer to FIG. 4 and FIG. 8), the driver monitor system 1 implements a steering concealment detection processing to modify control of imaging when steering concealment is detected. FIG. 11 is a flow chart showing the steering concealment detection processing. The processing of the flow chart shown in FIG. 11 is started, for example, when the driver monitor system 1 is started, and is implemented repeatedly at a constant interval. The processing of the flow chart shown in FIG. 11 is implemented simultaneously with the proximity detection processing of FIG. 4 or FIG. 8.

The projection determination unit 27 first determines whether the operation angle θ of the steering wheel 35 (FIG. 1) is greater than a predetermined threshold θth (S31), according to the signal from the steering angle sensor 28 (FIG. 1). The threshold θth is set at a value when the steering concealment may occur and may be specifically set as θth=30°. When the operation angle θ of the steering wheel 35 is less than or equal to the threshold θth (S31: No), it is determined that the possibility that the steering concealment occurs is low, and the processing of the flow chart shown in FIG. 11 is terminated.

To the contrary, when the operation angle θ of the steering wheel 35 is greater than the threshold θth (S31: Yes), it is determined that the steering concealment may occur, and the processing proceeds to S32. At S32, the image processing unit 25 retrieves the photographic image captured with the camera 22 (S32). Subsequently, the image processing unit 25 implements substantially the same recognition processing as that of S14 in FIG. 4 or FIG. 8 thereby to try to detect the face region and the background region from the photographic image (S33). Subsequently, the projection determination unit 27 determines whether the image processing unit 25 successfully detects the face region according to the signal sent from the image processing unit 25 (S34). When the image processing unit 25 successfully detects the face region (S34: Yes), it is determined that the steering concealment does not occur, and the processing of the flow chart shown in FIG. 11 is terminated. To the contrary, when the image processing unit 25 does not detect the face region (S34: No), it is highly possible that the steering concealment may occur, and the processing proceeds to S35.

At S35, the projection determination unit 27 calculates a rate R of the background region relative to the entire photographic image, according to the photographic image retrieved by S32 and the background region detected by the image processing unit 25 at S33 (S35). When the steering concealment occurs, an obstacle such as an arm of the driver may be located in front of the camera 22. Therefore, the photographic image includes an obstacle region corresponding to the obstacle. Consequently, the rate R of the background region becomes small due to the obstacle region. In consideration of this, the projection determination unit 27 determines whether the rate R of the background region is less than a predetermined threshold Rth (S36). The threshold Rth is set at, for example, a value less than 10%.

When the rate R of the background region is greater than or equal to the threshold Rth (S36: No), it is determined that the steering concealment does not occur, and the processing of the flow chart shown in FIG. 11 is terminated. In this case, although the camera 22 may successfully image the driver's face, the image processing unit 25 may be unable to detect the face region for a certain reason. To the contrary, when the rate R of the background region is less than the threshold Rth (S36: Yes), it is determined that the steering concealment may occur, and the processing proceeds to S37. in this case, the projection determination unit 27 notifies the imaging control unit 23 that the steering concealment occurs. Thus, the imaging control unit 23 increases the driving interval of the shutter of the camera 22 (S37). That is, the imaging control unit 23 increases the exposure interval, i.e., the cycle T1 of the pulse in FIG. 3. In this way, the imaging control unit 23 reduces the frame rate of the camera 22 (S37). Specifically, the imaging control unit 23 changes the frame rate of the camera 22 from, for example, 30 frames per second to 10 frames per second. As described above with reference to FIG. 3, the projection timing of light from the projector 21 is synchronized with the exposure timing of the camera 22. Therefore, the interval T2 (projection interval, FIG. 3) between activation of the projector 21 is increased, accompanied with the reduction in the frame rate of the camera 22. At S37, the projection control unit 24 may stop or dim light projected from the projector 21 thereby to reduce power of the light. With the present configuration, electronic components of the projector circuit can be restrained from aging. Thus, processing of the flow chart in FIG. 11 is terminated.

According to the present embodiment as described above, the frame rate of the camera 22 is reduced when the steering concealment occurs, thereby to increase the projection interval of the projector 21. Thus, continued meaningless imaging operation and continued meaningless projection of light can be restrained. In particular, increase in the projection interval enables reduction in energy loss and mitigation of driver's eyestrain.

In addition, the imaging with the camera 22 does not stop imaging when the steering concealment occurs. Therefore, it can be determined whether the steering concealment continues or ends according to the photographic image captured with the camera 22 subsequently. Thus, when the steering concealment ends, the original exposure timing and the original projection timing can be resumed.

Fourth Embodiment

Figure 12:
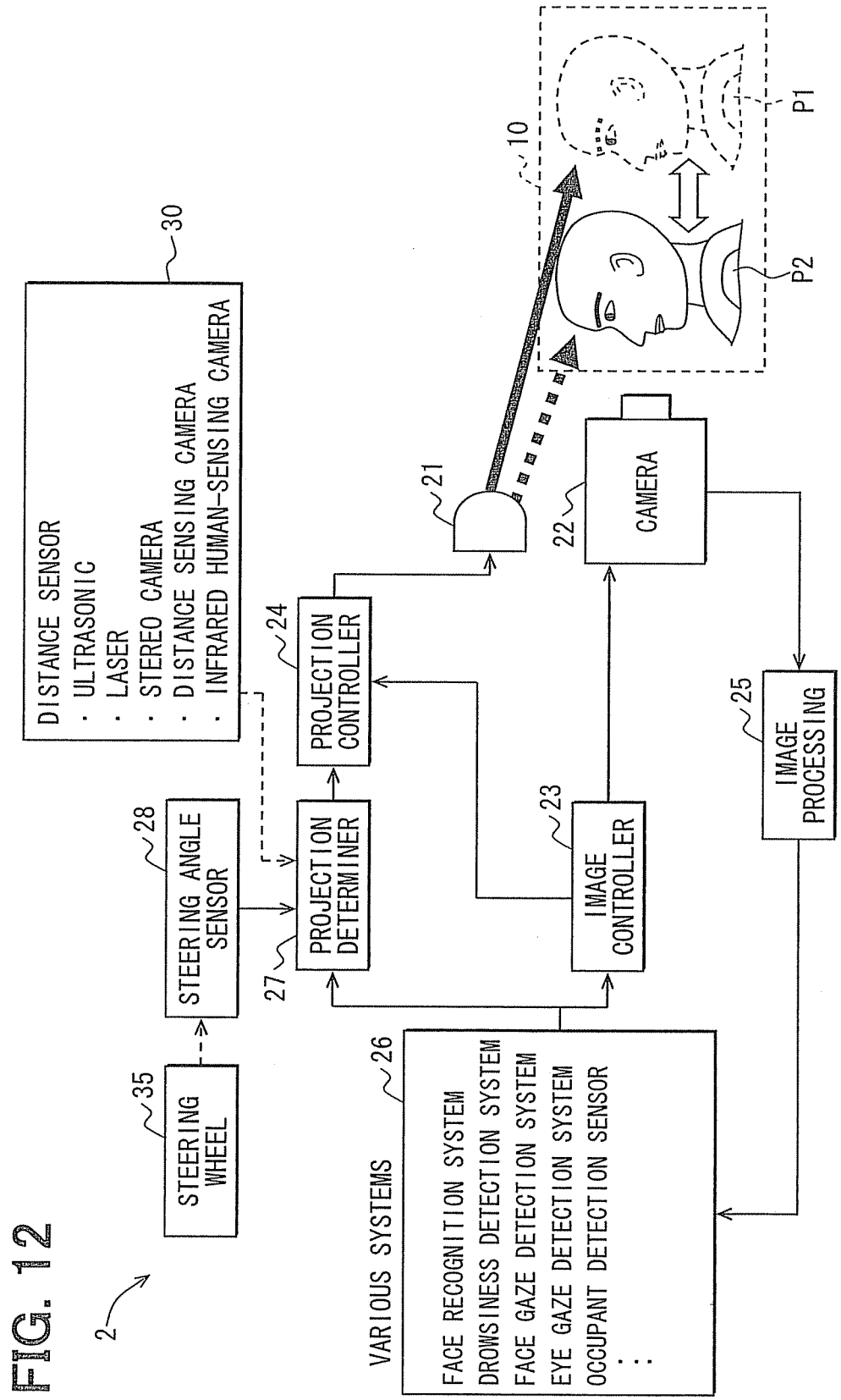
FIG. 12 is an overview showing a driver monitor system according to the fourth embodiment.
Figure 13:
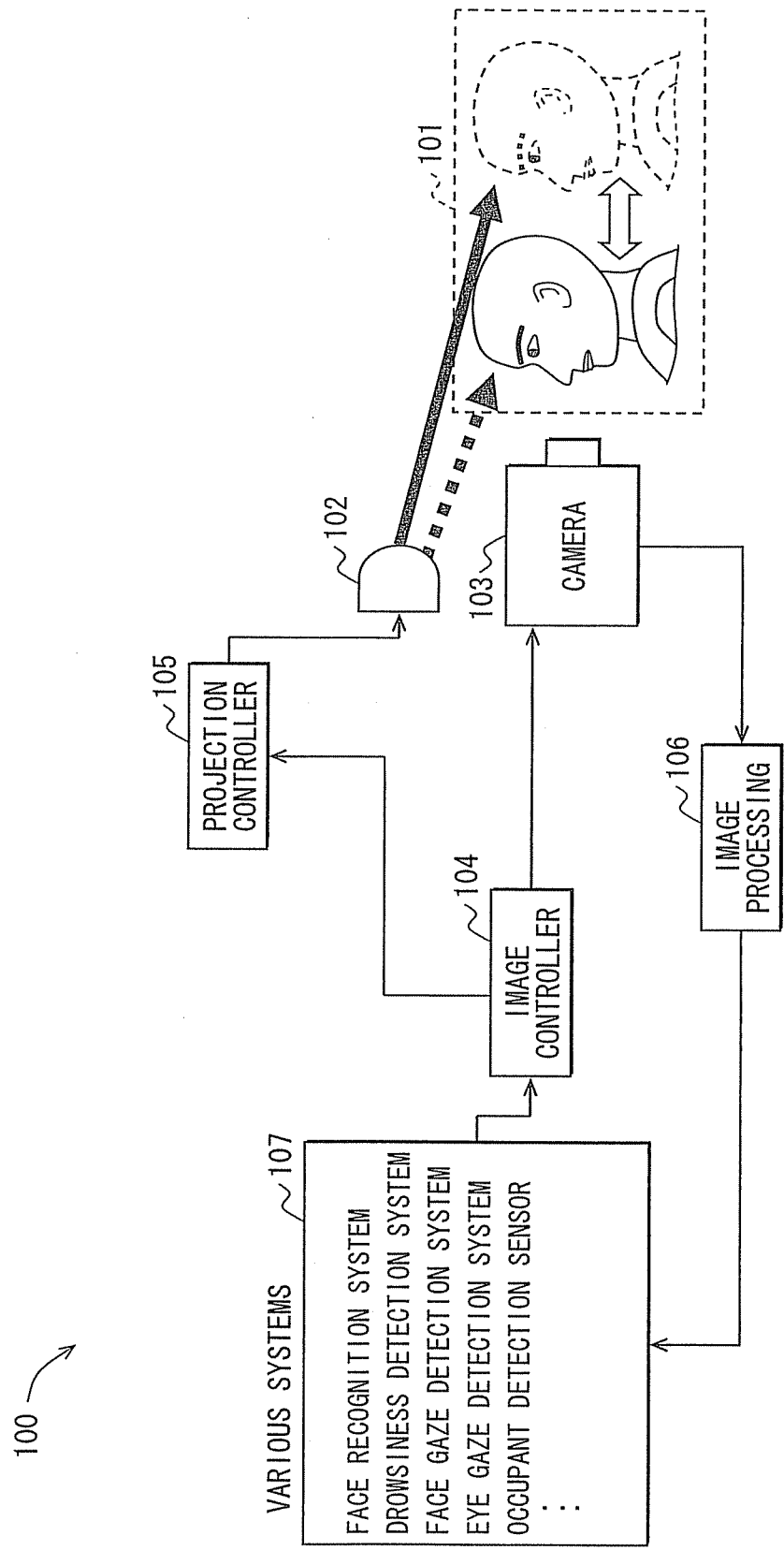
FIG. 13 is an overview showing a driver monitor system according to a prior art.

Subsequently, the face imaging system according to the fourth embodiment will be described. As follows, difference of the face imaging system from the above embodiments will be mainly described. FIG. 12 shows an overview of the driver monitor system 2 according to the present embodiment. In FIG. 12B, equivalent parts to those in FIG. 1 are denoted by the same reference numerals. The configuration of the driver monitor system 2 shown in FIG. 12 including a distance sensor 30 differs from the driver monitor system 1 shown in FIG. 1.

The distance sensor 30 is configured to detect the distance from an object, which exists around the projector 21. In the present configuration, various kinds of generally-known distance sensors are employable as the distance sensor 30. For example, the distance sensor 30 may be a sensor configured to emit an ultrasonic wave or a laser beam therearound to detect the distance from an object according to a reflective wave. Alternatively, the distance sensor 30 may be a sensor configured to detect the distance according to a stereo image or may be a sensor configured to detect the distance by perceiving an infrared ray radiated from an object within a specific distance. The configuration of the distance sensor 30 is determined to enable the distance sensor 30 to detect the distance from an object such as the driver's face around the projector 21. More specifically, the configuration of the distance sensor 30, such as the mount position and/or the emission area of the signal of an ultrasonic wave and/or a laser beam, is determined to enable the distance sensor 30 to detect the distance from, in particular, an object in the driver's seat peripheral region 10.

The distance sensor 30 is configured to send its detection signal to the projection determination unit 27. The projection determination unit 27 determines whether the driver's face approaches the projector 21 according to the detection signal from the distance sensor 30, in addition to the processing results of the photographic image in the above embodiments. Specifically, in the present embodiment, the proximity detection processing of FIG. 4 or FIG. 8 further includes a processing to determine whether the distance detected with the distance sensor 30 is less than a predetermined threshold, subsequent to the processing of S20 in the case of FIG. 4 or subsequent to the processing of S27 in the case of FIG. 8. Subsequently, on determination of proximity of the driver's face when the detection distance is less than the threshold, projection of light from the projector 21 is stopped or dimmed (S21). With the present configuration, proximity of the driver's face can be detected with high accuracy. The single device of the distance sensor 30 may be configured to detect proximity of the driver's face.

The above-described embodiments may be arbitrary modified as follows. For example, in the above embodiments, the face imaging system is exemplified with the driver monitor system configured to image the driver's face. It is noted that the face imaging system may be applied to a system to image a users' face other than or in addition to the driver's face.

In the above embodiments, the projector 21 may be equivalent to a projection unit. The camera 22 may be equivalent to an imaging unit. The imaging control unit 23, the projection control unit 24, the image processing unit 25, and the projection determination unit 27 configured to implement the processing of S11 to S23 in FIG. 4, the processing of S11 to S27 in FIG. 8, or the processing of S11 to S29 in FIG. 10 may be equivalent to a proximity detection unit. The projection control unit 24 configured to implement the processing of S21 in FIG. 4, FIG. 8, or FIG. 10 may be equivalent to the first lighting control unit. The projection determination unit 27 configured to implement the processing S16 to S18 in FIG. 4 or the processing of S24, S25 in FIG. 8 may be equivalent to an edge extraction unit. The projection determination unit 27 configured to implement the processing of S19 and S20 in FIG. 4 or the processing of S26 and S27 in FIG. 8 may be equivalent to an edge determination unit. The image processing unit 25 configured to implement the processing of S14 in FIG. 4, FIG. 8, or FIG. 10 may be equivalent to a face recognition unit. The imaging control unit 23 in FIG. 1 may be equivalent to an imaging control unit (device). The projection control unit 24 in FIG. 1 may be equivalent to a second projection control unit (device). In addition to the steering angle sensor 28, the imaging control unit 23, the projection control unit 24, the image processing unit 25, and the projection determination unit 27 configured to implement the processing of S31 to S36 in FIG. 11 may be equivalent to a concealment detection unit. The distance sensor 30 in FIG. 12 may be equivalent to a distance detection unit. The projection determination unit 27 configured to implement the processing of S22 in FIG. 4 or in FIG. 8 may be equivalent to a blooming region detection unit. The projection determination unit 27 configured to implement the processing of S23 in FIG. 4 or in FIG. 8 may be equivalent to a black crushing detection unit.

Summarizing the above embodiments, the face imaging system includes: the projection unit configured to project light to the projection region predetermined as the region in which the user's face is supposed to be located; the imaging unit configured to image the region including the projection region projected with light from the projection unit; the proximity detection unit configured to detect that the user's face approaches the projection unit; and the first projection control unit configured to cause the projection unit to stop or dim projection of light when the proximity detection unit detects the approach.

With the present configuration, the proximity detection unit is configured to detect that the user's face approaches the projection unit. In this case, the first projection control unit causes the projection unit to stop or dim light thereby to mitigate eyestrain caused in user's eyes.

In addition, the proximity detection unit may be further configured to detect the approach according to the photographic image captured with the imaging unit.

With the present configuration, when the user's face approaches the projection unit, the photographic image can be obtained according to the approach. Therefore, the proximity detection unit is capable of detecting that the user's face approaches the projection unit according to the photographic image. With the present configuration, another sensor for detecting approach of the user's face need not be additionally provided. Therefore, the configuration of the face imaging system can be simplified.

The imaging unit may have the lens structure configured to cause blur in the region corresponding to the object in the photographic image when imaging the object approaching the projection unit. In this case, the face imaging system may further include the edge extraction unit configured to extract edge information from the photographic image, the edge information reflecting a feature of an edge in the photographic image. In addition, the face imaging system may further include the edge determination unit configured to determine whether the edge information extracted with the edge extraction unit is edge information with blur.

With the present configuration, the imaging unit includes the lens structure configured to generate blur in the imaging region corresponding to the object when imaging the object approaching the projection unit. Therefore, blur can be generated in the photographic image when a user approaches the projection unit. In this case, the edge information extracted with the edge extraction unit becomes edge information reflecting blur. Further, in this case, the edge determination unit determines that the extracted edge information is the edge information with blur thereby to detect proximity (approach) of the user's face. In this way, the proximity (approach) is detected according to the edge information. Thereby, even in the case where the user's face cannot be detected, proximity of the user's face is detectable.

The imaging unit may be further configured to image the projection region in a form to image the surrounding structure, which does not change in position relative to the imaging unit. In this case, the edge determination unit may be further configured to compare the edge information on the background region, which is the region corresponding to the structure in the photographic image, with the edge information on the unfixed region, which is the region other than the background region, thereby to determine whether the edge information on the unfixed region is edge information with blur.

With the present configuration, the imaging unit obtains the photographic image of the surrounding structure. Therefore, the photographic image includes the background region corresponding to the structure. The structure does not change in the position relative to the imaging unit. Therefore, the edge information in the background region is the edge information without blur. In addition, the unfixed region other than the background region in the photographic image includes the face region corresponding to the user's face. Therefore, when the user's face approaches, the edge information in the unfixed region becomes the edge information reflecting blur. In this case, the edge information in the unfixed region includes a different feature from that of the edge information in the background region. To the contrary, when the user's face does not approach, the edge information in the unfixed region includes a feature similar to that of the edge information in the background region. Therefore, the edge determination unit is capable of determining whether the edge information in the unfixed region is the edge information with blur by comparing the edge information in the unfixed region with the edge information in the background region. Thus, determination whether blur occurs in the photographic image can be made, and furthermore, determination whether the user's face approaches can be made, according to the comparison result of the edge information in the unfixed region with the edge information in the known region (background region) without blur, in this way.

The edge determination unit may be further configured to compare the present edge information with the previous edge information on the previous photographic image without blur thereby to determine whether the present edge information is edge information with blur.

When blur occurs in the present photographic image, the present edge information changes from the previous edge information on the previous photographic image without blur. To the contrary, when blur does not occur in the present photographic image, the present photographic image does not have a large difference from the previous edge information. Therefore, determination whether the present edge information is the edge information with blur can be made according to the comparison result of the present edge information with the previous edge information.

The face imaging system may further include the face recognition unit configured to detect the face region in the photographic image, the face region being the region corresponding to the user's face. In this case, the proximity detection unit may be further configured to detect the approach according to the size of the face region when the face recognition unit detects the face region.

With the present configuration, it is deemed that the size of the face region corresponding to the user's face in the photographic image correlates with the proximity (approach) of the user's face to the projection unit. Therefore, when the face recognition unit successfully detects the face region, the proximity detection unit is capable of detecting the proximity of the user's face according to the size of the face region. Thus, proximity of the user's face is detectable without use of the edge information.

The face imaging system may further include: the imaging control unit configured to control the exposure condition of the imaging unit; the second projection control unit configured to control the projection timing of light from the projection unit according to the exposure timing of the imaging unit; and the concealment detection unit configured to detect that the imaging unit is concealed with an obstacle according to the photographic image. In this case, when the concealment detection unit detects the concealment, the imaging control unit may increase the exposure interval of the imaging unit and/or the first projection control unit may cause the projection unit to stop projection of light or to dim projection of light.

With the present configuration, the second projection control unit is capable of associating the projection timing of light from the projection unit with the exposure timing of the imaging unit. With the present configuration, the projection unit projects light, while the imaging unit opens its shutter to implement imaging. Furthermore, an obstacle may conceal the imaging unit to disable imaging of the user's face due to the obstacle. In this case, it may cause waste to continue obtaining the photographic images and to continue projection of light. With the present configuration, when the concealment detection unit detects concealment of the imaging unit according to the photographic image. Further, the imaging control unit increases the exposure interval, when concealment of the imaging unit is detected. In addition or alternatively, the first projection control unit may stop or dim the projection of light thereby to reduce the power of the projected light. In connection with increase in the exposure interval, the projection interval of the projection unit also increases. Therefore, energy loss caused by meaningless projection of light can be restrained, and eyestrain caused in the user's eyes can be mitigated. In addition, electronic components of the projector circuit can be restrained from aging. In addition, the imaging unit does not stop imaging when the concealment of the imaging unit occurs. Therefore, determination whether the concealment of the imaging unit continues or ends can be made, according to the photographic image captured with the imaging unit subsequently. Thus, when the concealment ends, the original exposure timing and the original projection timing can be resumed.

The proximity detection unit may include the distance detection unit configured to detect the distance of an object, which exists around the projection unit. In this case, the proximity detection unit may be further configured to detect that the object approaches the projection unit according to the distance detected with the distance detection unit. The distance detection unit may be, for example, an ultrasonic wave, a camera configured to detect the distance, and/or a laser.

With the present configuration, proximity of an object such as the user's face is detectable without use of the photographic image. Alternatively, proximity of the user's face is detectable with high accuracy by combining the detection of proximity according to the photographic image and the detection of proximity with the distance detection unit.

The face imaging system may further include the blooming region detection unit configured to detect that: the blooming region (blooming photo) occurs entirely in pixels around the center of the photographic image; or pixel values of pixels entirely around the center of the photographic image becomes greater than or equal to the first threshold, which is predetermined as a value equivalent to the blooming region. In this case, the proximity detection unit may be further configured to deem that the user's face approaches the projection unit when the blooming region detection unit detects the blooming region or detects that the pixel values become greater than or equal to the first threshold.

When the user's face approaches the imaging unit rapidly without passing through the blur state, the imaging unit may capture an image strongly reflecting light from the projection unit. In this case, the captured image around the center of the photographic image may become substantially pure white unclear image in the blooming state. With the present configuration, the proximity detection unit determines that proximity of the user's face occurs also, when the blooming region detection unit detects the blooming region. Therefore, even in the case of rapid proximity without passing through the blur state, the first projection control unit is capable of causing the projection unit to stop or dim projected light. In addition, the blooming region detection unit may be further configured to detect that the pixel values around the center of the photographic image become greater than or equal to the first threshold predetermined as a value equivalent to the blooming region, in addition to or alternatively to detection of the blooming region. In this case, the proximity detection unit may also determine proximity of the user's face. With the present configuration, even in the case where the imaging mode of the imaging unit is in, for example, the high dynamic range mode (HDR mode) hardly to cause the blooming region, proximity of the face can be detected, and lighting can be stopped or dimmed.

The face imaging system may further include the black crushing detection unit configured to detect that: the black crushing (black crushing photo) occurs entirely in pixels around the center of the photographic image; or the pixel values of pixels entirely around the center of the photographic image become less than or equal to the second threshold, which is predetermined as the value equivalent to the black crushing. In this case, the proximity detection unit may be further configured to deem that the user's face approaches the projection unit when the black crushing detection unit detects the black crushing or detects that the pixel values become less than or equal to the second threshold.

When the user's face in the blooming state further approaches the imaging unit, the imaging unit is substantially covered to be in the black-crushing state in which the imaging unit captures a black crushing image. With the present configuration, the black crushing detection unit is configured to detect the black crushing, and the proximity detection unit determines proximity of the user's face occurs also, when the black crushing detection unit detects the black crushing. Therefore, in this case, the projection of light can be stopped or dimmed. Similarly to the case of the blooming region, determination of proximity of the user's face is made also when the pixel values around the center of the photographic image becomes less than or equal to the second threshold, which is predetermined at a small value equivalent to the black crushing image. Thus, even in the case where the imaging unit has high sensitivity hardly to cause the black crushing, lighting can be stopped or dimmed.

The face may be an eye. In this case, when light is projected to user's eyes and when the user's eyes approach the projection unit, projection of light is stopped or dimmed, thereby to mitigate eyestrain caused in the user's eyes.

The imaging unit may have a lens configuration configured to cause blur in a region in which a depth of field is less than or equal to 20 cm.

The imaging unit may have a lens configuration configured to decrease modulation transfer function (MTF) in a specific region.

The proximity detection unit may be further configured to: sample temperature information on temperature of a lens of the imaging unit; and change a detection condition of approach of the user's face according to the sampled temperature information.

The above structures of the embodiments can be combined as appropriate. The above processings such as calculations and determinations are not limited being executed by the processing units 23 to 27. The control unit may have various structures including the processing units 23 to 27 shown as an example.

The number of the components and the objects related to the face imaging system may be determined arbitrary from one or from two or more. Specifically, the device, such as the projection unit, the imaging unit, the detection unit, and the control unit, may be one and may be two or more. In addition, the object, such as the region, the face, and the background, may be one and may be two or more.

The above processings such as calculations and determinations may be performed by any one or any combinations of software, an electric circuit, a mechanical device, and the like. The software may be stored in a storage medium, and may be transmitted via a transmission device such as a network device. The electric circuit may be an integrated circuit, and may be a discrete circuit such as a hardware logic configured with electric or electronic elements or the like. The elements producing the above processings may be discrete elements and may be partially or entirely integrated.

It should be appreciated that while the processes of the embodiments of the present invention have been described herein as including a specific sequence of steps, further alternative embodiments including various other sequences of these steps and/or additional steps not disclosed herein are intended to be within the steps of the present invention.

Various modifications and alternations may be diversely made to the above embodiments without departing from the spirit of the present invention.

What is claimed is:

1. A face imaging system comprising:
   a projection unit configured to project light to a predetermined projection region in which a user's face is supposed to be located;
   an imaging unit configured to image a region including the projection region projected with the light from the projection unit;
   a proximity detection unit configured to detect approach of the user's face, according to an image captured with the imaging unit, relative to the projection unit; and
   a first projection control unit configured to cause the projection unit to stop or dim projection of the light when the proximity detection unit detects the approach of the user's face, wherein
   the imaging unit has a lens structure configured to cause blur in a region corresponding to an object in the image when the object approaches the projection unit,
   the proximity detection unit includes:
      an edge extraction unit configured to extract edge information from the image, the edge information reflecting a feature of an edge in the image, and
      an edge determination unit configured to determine whether the edge information extracted with the edge extraction unit has blur,
   the imaging unit is further configured to image the projection region to include a surrounding structure being constant in position relative to the imaging unit,
   the edge determination unit is further configured to make a comparison between the edge information on a background region corresponding to the surrounding structure in the image and the edge information on an unfixed region other than the background region, thereby to determine whether the edge information on the unfixed region has blur; and the face imaging system further comprises:
   a blooming region detection unit configured to detect that:
      a blooming region occurs entirely in pixels around a center of the image; or
      pixel values of the pixels entirely around the center of the image become greater than or equal to a blooming threshold, which is a predetermined large value representing the blooming region, wherein
   the proximity detection unit is further configured to determine that the user's face approaches the projection unit when the blooming region detection unit detects the blooming region or detects that the pixel values become greater than or equal to the blooming threshold.

2. A face imaging system comprising:
   a projection unit configured to project light to a predetermined projection region in which a user's face is supposed to be located;
   an imaging unit configured to image a region including the projection region projected with the light from the projection unit;
   a proximity detection unit configured to detect approach of the user's face, according to an image captured with the imaging unit, relative to the projection unit;
   a first projection control unit configured to cause the projection unit to stop or dim projection of the light when the proximity detection unit detects the approach of the user's face;
   an imaging control unit configured to control an exposure condition of the imaging unit;
   a second projection control unit configured to control a projection timing of the light from the projection unit according to an exposure timing of the imaging unit; and
   a concealment detection unit configured to detect concealment of the imaging unit with an obstacle according to the image, wherein
   when the concealment detection unit detects the concealment of the imaging unit:
      the imaging control unit increases an exposure interval of the imaging unit; and/or
      the first projection control unit causes the projection unit to stop projection of the light or to dim the projection of the light; and the face imaging system further comprises:

a blooming region detection unit configured to detect that:
   a blooming region occurs entirely in pixels around a center of the image; or
   pixel values of the pixels entirely around the center of the image become greater than or equal to a blooming threshold, which is a predetermined large value representing the blooming region, wherein
the proximity detection unit is further configured to determine that the user's face approaches the projection unit when the blooming region detection unit detects the blooming region or detects that the pixel values become greater than or equal to the blooming threshold.

3. A face imaging system comprising:
a projection unit configured to project light to a predetermined projection region in which a user's face is supposed to be located;
an imaging unit configured to image a region including the projection region projected with the light from the projection unit;
a proximity detection unit configured to detect approach of the user's face, according to an image captured with the imaging unit, relative to the projection unit;
a first projection control unit configured to cause the projection unit to stop or dim projection of the light when the proximity detection unit detects the approach of the user's face; and
a black crushing detection unit configured to detect that:
black crushing occurs entirely in pixels around a center of the image; or
pixel values of the pixels entirely around the center of the image become less than or equal to a black crushing threshold, which is a predetermined small value representing the black crushing, wherein
the proximity detection unit is further configured to determine that the user's face approaches the projection unit when the black crushing detection unit detects the black crushing or detects that the pixel values become less than or equal to the black crushing threshold.

4. The face imaging system according to claim 1, further comprising:
a face recognition unit configured to detect a face region corresponding to the user's face in the image, wherein
the proximity detection unit is further configured to detect the approach of the user's face according to a size of the face region when the face recognition unit detects the face region.

5. The face imaging system according to claim 1, wherein
the proximity detection unit includes a distance detection unit configured to detect a distance of the object in the projection region, and
the proximity detection unit is further configured to detect approach of the object relative to the projection unit according to the distance detected with the distance detection unit.

6. The face imaging system according to claim 1, wherein the approach of the user's face is approach of an eye of the user.

7. The face imaging system according to claim 2, further comprising:
a face recognition unit configured to detect a face region corresponding to the user's face in the image, wherein
the proximity detection unit is further configured to detect the approach of the user's face according to a size of the face region when the face recognition unit detects the face region.

8. The face imaging system according to claim 2, wherein
the proximity detection unit includes a distance detection unit configured to detect a distance of an object in the projection region, and
the proximity detection unit is further configured to detect approach of the object relative to the projection unit according to the distance detected with the distance detection unit.

9. The face imaging system according to claim 3, further comprising:
a face recognition unit configured to detect a face region corresponding to the user's face in the image, wherein
the proximity detection unit is further configured to detect the approach of the user's face according to a size of the face region when the face recognition unit detects the face region.

10. The face imaging system according to claim 3, wherein
the proximity detection unit includes a distance detection unit configured to detect a distance of an object in the projection region, and
the proximity detection unit is further configured to detect approach of the object relative to the projection unit according to the distance detected with the distance detection unit.

11. The face imaging system according to claim 3, further comprising:
a blooming region detection unit configured to detect that:
   blooming region occurs entirely in pixels around a center of the image; or
   pixel values of the pixels entirely around the center of the image become greater than or equal to a blooming threshold, which is a predetermined large value representing the blooming region, wherein
the proximity detection unit is further configured to determine that the user's face approaches the projection unit when the blooming region detection unit detects the blooming region or detects that the pixel values become greater than or equal to the blooming threshold.

* * * * *